(12) United States Patent
Caltabiano et al.

(10) Patent No.: US 9,907,767 B2
(45) Date of Patent: Mar. 6, 2018

(54) PHARMACEUTICAL COMPOSITIONS AND THE TREATMENT OF OVERACTIVE BLADDER

(71) Applicant: VELICEPT THERAPEUTICS, INC., Malvern, PA (US)

(72) Inventors: Stephen Caltabiano, King of Prussia, PA (US); Eliot Ohlstein, Glenmore, PA (US); Stewart McCallum, King of Prussia, PA (US)

(73) Assignee: Velicept Therapeutics, Inc., Malvern, PA (US)

( * ) Notice: Subject to any disclaimer, the term of this patent is extended or adjusted under 35 U.S.C. 154(b) by 0 days.

(21) Appl. No.: 15/323,685

(22) Filed: Jan. 3, 2017

(65) Prior Publication Data

US 2017/0151199 A1    Jun. 1, 2017

Related U.S. Application Data

(63) Continuation-in-part of application No. PCT/US2015/038583, filed on Jun. 30, 2015, which is a continuation-in-part of application No. 15/235,720, filed on Aug. 12, 2016, which is a continuation of application No. 13/762,563, filed on Feb. 8, 2013, now Pat. No. 9,522,129.

(60) Provisional application No. 62/020,889, filed on Jul. 3, 2014, provisional application No. 61/596,893, filed on Feb. 9, 2012.

(51) Int. Cl.
*A61K 31/44* (2006.01)
*A61K 31/24* (2006.01)
*A61K 31/135* (2006.01)
*A61K 31/196* (2006.01)
*A61K 31/216* (2006.01)

(52) U.S. Cl.
CPC .......... *A61K 31/196* (2013.01); *A61K 31/216* (2013.01)

(58) Field of Classification Search
CPC ... A61K 31/135; A61K 31/137; C07D 453/02
USPC ................... 514/650, 305, 534, 646
See application file for complete search history.

(56) References Cited

U.S. PATENT DOCUMENTS

| | | | |
|---|---|---|---|
| 4,478,849 A | 10/1984 | Ainsworth et al. | |
| 4,772,631 A | 9/1988 | Holloway et al. | |
| 6,069,176 A | 5/2000 | Tsuchiya et al. | |
| 6,123,961 A | 9/2000 | Aberg | |
| 6,251,925 B1 | 6/2001 | Donaldson et al. | |
| 6,395,762 B1 | 5/2002 | Fobare et al. | |
| 6,444,685 B1 | 9/2002 | Sum et al. | |
| 6,451,814 B1 | 9/2002 | Ashwell et al. | |
| 6,548,523 B2 | 4/2003 | Lawrence et al. | |
| 7,022,716 B2 | 4/2006 | Hu et al. | |
| 7,034,053 B2 | 4/2006 | Deaton et al. | |
| 7,425,639 B2 | 9/2008 | Cooke et al. | |
| 7,709,677 B2 | 5/2010 | Cooke et al. | |
| 8,017,613 B2 | 9/2011 | Scilimati et al. | |
| 8,247,415 B2 | 8/2012 | Berger et al. | |
| 8,354,403 B2 | 1/2013 | Edmondson et al. | |
| 8,399,408 B2 | 3/2013 | Austen et al. | |
| 8,642,661 B2 | 2/2014 | Caltabiano et al. | |
| 9,522,129 B2 | 12/2016 | Caltabiano et al. | |
| 2003/0082230 A1 | 5/2003 | Baichwal et al. | |
| 2004/0122014 A1 | 6/2004 | Mammen et al. | |
| 2005/0101607 A1 | 5/2005 | Michel et al. | |
| 2005/0154041 A1 | 7/2005 | Michel et al. | |
| 2005/0181031 A1* | 8/2005 | Saito ................. | A61K 31/4745 424/448 |
| 2005/0261328 A1 | 11/2005 | Wienrich et al. | |
| 2005/0261369 A1 | 11/2005 | Mehlburger et al. | |
| 2006/0084700 A1 | 4/2006 | Michel | |
| 2007/0078181 A1 | 4/2007 | Michel | |
| 2009/0253705 A1 | 10/2009 | Berger et al. | |
| 2010/0240697 A1 | 9/2010 | Suzuki et al. | |
| 2010/0286275 A1 | 11/2010 | Zhang | |
| 2010/0291209 A1 | 11/2010 | Vergnault et al. | |
| 2011/0028461 A1 | 2/2011 | Berger et al. | |
| 2011/0081426 A1 | 4/2011 | Rao et al. | |
| 2012/0035118 A1 | 2/2012 | Caltabiano et al. | |
| 2012/0053181 A1 | 3/2012 | Lin et al. | |
| 2012/0142725 A1 | 6/2012 | Van Charldorp et al. | |
| 2012/0157432 A1 | 6/2012 | Edmondson et al. | |

(Continued)

FOREIGN PATENT DOCUMENTS

EP    0400519 A    12/1990
EP    0455006 A    11/1991

(Continued)

OTHER PUBLICATIONS

"Gynecological Urology", Le MA ed. Science Press, Aug. 2009, Edition 1, pp. 323-330.
Abrams et al. "Combination treatment with mirabegron and solifenacin in patients with overaactive bladder (OAB) efficacy results from a phase 2 study (Symphony)" May 4-8, 2013 AUA Annual Meeting, San Diego, CA (abstract only).
Arch et al. "Atypical β0adrenoceptor on brown adipocytes as target for anti-obesity drugs" May 10, 1984, Nature 309:163-165.
Bianchetti et al. "In vitro inhibition of intestinal motiliy by phenylethanolaminotetralines: evidence of atypical βadrenoceptors in rat colon" Aug. 1990, Br. J. Pharmacol. 100:831-839.
Definition of "compound" and "composition" from the Grant & Hackh's Chemical Dictionary, 1987, McGraw-Hill, Inc., p. 148.

(Continued)

*Primary Examiner* — Raymond J Henley, III
(74) *Attorney, Agent, or Firm* — Pepper Hamilton LLP

(57) ABSTRACT

The present invention relates to methods of treating overactive bladder and the symptoms associated therewith, for example, urinary urgency, frequency of mictruitions, nocturia, and urgency urinary incontinence. One treatment method according to the present invention comprises treatment with the beta-3 adrenergic receptor agonist solabegron. Another treatment combination according to the invention comprises solabegron, and a muscarinic receptor antagonist which results in a synergistic effect on the symptoms associated with OAB.

42 Claims, 5 Drawing Sheets

(56) References Cited

U.S. PATENT DOCUMENTS

| | | | |
|---|---|---|---|
| 2012/0225886 A1 | 9/2012 | Edmundson et al. | |
| 2012/0258963 A1 | 10/2012 | Berger et al. | |
| 2012/0289565 A1* | 11/2012 | Paborji | A61K 31/137 514/397 |
| 2013/0053403 A1 | 2/2013 | Berger et al. | |
| 2013/0172277 A1 | 7/2013 | Caltabiano et al. | |
| 2014/0243544 A1 | 8/2014 | Wang et al. | |
| 2015/0306170 A1 | 10/2015 | Ahuja et al. | |
| 2016/0158176 A1* | 6/2016 | Ohlstein | A61K 9/2081 424/472 |
| 2017/0035716 A1* | 2/2017 | Ohlstein | A61K 45/06 |
| 2017/0151199 A1 | 6/2017 | Caltabiano et al. | |
| 2017/0348263 A1 | 12/2017 | Ohlstein et al. | |
| 2017/0348288 A1 | 12/2017 | Ohlstein et al. | |

FOREIGN PATENT DOCUMENTS

| | | |
|---|---|---|
| EP | 0543662 A | 5/1993 |
| EP | 0806948 B1 | 9/2000 |
| EP | 1258253 A1 | 11/2002 |
| EP | 1967202 A1 | 9/2008 |
| EP | 2216021 A1 | 8/2010 |
| GB | 940540 | 10/1963 |
| WO | 1995033724 A | 12/1995 |
| WO | 1999065877 A1 | 12/1999 |
| WO | 2001042195 A1 | 6/2001 |
| WO | 2001054728 A1 | 8/2001 |
| WO | 2003024483 A1 | 3/2003 |
| WO | 2004041806 A2 | 5/2004 |
| WO | 2004047838 A2 | 6/2004 |
| WO | 2005065673 A1 | 7/2005 |
| WO | 2005067938 A1 | 7/2005 |
| WO | 2006113649 A1 | 10/2006 |
| WO | 2008121268 A1 | 10/2008 |
| WO | 2009057685 A1 | 5/2009 |
| WO | 2009124167 A1 | 10/2009 |
| WO | 2010118291 A2 | 10/2010 |
| WO | 2011025690 A1 | 3/2011 |
| WO | 2011043942 A1 | 4/2011 |
| WO | 2012018773 A1 | 2/2012 |
| WO | 2013119910 A1 | 8/2013 |
| WO | 2014034860 A1 | 3/2014 |
| WO | 2015120110 A2 | 8/2015 |
| WO | 2016004056 A1 | 1/2016 |
| WO | 2017070689 A2 | 4/2017 |
| WO | 2017210696 A1 | 12/2017 |
| WO | 2017210700 A1 | 12/2017 |

OTHER PUBLICATIONS

Ellsworth et al. "Solabegron: a Potential Future Addition to the β-3 Adrenoceptor Agonist Armamentarium for the Management of Overacative Bladder" (Mar. 5, 2015) Expert Opinion on Investig. Drugs 24(3):413-419.

Emorine et al. "Molecular characterization of the human beta 3-adrenergic receptor" Sep. 8, 1989, Science 245(4922):1118-1121.

Gillespie et al. "Modulation of non-voiding activity by the muscarinergic antagonist tolterodine and the Beta-3-adrenoceptor agonist mirabegron in conscious rats with partial outflow obstruction" 2012, BJU International 110:E132-E142.

Hertzberg et al. "Synthesis of the β3-adrenergic Receptor Agonist Solabegron and Analogous N-(2-ethylamino)-β-amino Alcohols from O-Acylated Cyanohydrins—Expanding the Scope of Minor Enantiomer Recycling" (Feb. 17, 2015) J. Organic Chem. 80(5):2937-2941.

Hicks et al. "GW427353 (solabegron), a novel, selective beta(3)-Adrenergic receptor agonist, evokes blader relaxation and increases micturition reflex threshold in the dog" Oct. 2007, J. of Pharmacol. and Experimental Therap. 323(1):202-209 (XP000002658787, ISSN: 002-3565).

Hutchinson et al. "β3-Adrenoceptor regulation and relaxation responses in mouse ileum" 2000, Br. J. Pharmacol. 129:1251-1259.

International Search Report and Written Opinion for PCT/US2011/046208 dated Sep. 26, 2011.

International Search Report and Written Opinion for PCT/US2013/025285 dated Mar. 25, 2013.

International Search Report and Written Opinion for PCT/US2015/063795 dated Feb. 11, 2016.

International Search Report and Written Opinon for PCT/US2015/038583 dated Sep. 17, 2015.

International Search Report and Written Opinion for PCT/US2016/058516 dated Jun. 5, 2017.

Otsuka et al. "Combination Effect of B3-Adrenoceptor Agonist and Muscarinic Receptor Antagonist on Human Detrusor Muscle Relaxation in Vitro" Oct. 2012, International Continence Society Meeting, pp. 894-895.

Product Label for Myrbetriq™ (mirabegron) Jun. 2012.

Product Label for VESIcare™ (solifenacin succinate) Apr. 2010.

Rackley et al. "Nighttime Dosing with Tolterodine Reduces Overactive Bladder-Related Nocturnal Micturitions in Patients with Overactive Bladder and Nocturia" 2006, Urology 67:731-736.

Singapore Search Report for SG 11201404776P dated Jul. 8, 2015.

Biers et al., The effects of a new selective β3-adrenoceptor agonist (GW427353) on spontaneous activity and detrusor relaxation in human bladder, Journal Compilation, 2006 BJU International (2006), 98:1310-1314.

Grudell et al. "Dose-response effect of a Beta-3-adrenergic Receptor Agonist, Solabegron, on Gastrointestinal Transit, Bowel Function, and Somatostatin Levels in Health" May 1, 2008, Am. J. Physiol.—Gastro. Liver Physiol. 294(5):G1114-G1119.

clinical trials.gov "Alternating Thalidomide and Lenalidomide Plus Rituximab as Initial Treatment for CLL" NCT01125176 May 17, 2010 (retrieved on Aug. 12, 2017). Retrieved from the internet; URL: <https://clinicaltrials.gov/archive/NCT0112,5176/2010_05_17> pp. 1-4; p. 1, brief summary and detailed description.

Irwin et al., Prevalence, Severity, and Symptom Bother of Lower Urinary Tract Symptoms among Men in the EPIC Study: Impact of Overactive Bladder, European Urology (Mar. 3, 2009), 56:14-20.

NCT00501267: "A Study to Test the Interaction of Two Medications for the Treatment of Overactive Bladder" available at https://clinicaltrials.gov/ct2/show/NCT00501267?term=NCT00501267&rank=1 (as retrieved on Feb. 15, 2016).

Ohlstein et al., A Multicenter, Double-blind, Randomized, Placebo-controlled Trial of the β3-Adrenoceptor Agonist Solabegron for Overactive Bladder, European Urology (Jun. 5, 2012), 62:834-840.

Vrydag et al. "Do gene polymorphisms alone or in combination affect the function of human β-adrenoceptors?" 2009, Br. J. Pharmacol. 156:127-134.

Lee, J et al.)"Effects of Food Intake on the Pharmacokinetic Properties of Mirabegron Oral 5, 10-18 Controlled-Absorption System: A Single Dose, Randomized, Crossover Study in Healthy Adults" Clinical Therapeutics 2013, vol. 35, No. 3, pp. 333-341; pp. 334, left column, second-third paragraphs; p. 335, left column, third paragraph; p. 337.

clinical trials.gov, "Thalidomide, Lenalidomide, and Rituximab for Previously Treated Waldenstrom Macroglobulinemia" NCT01779167, May 26, 2017 (retrieved Sep. 5, 2017 from URL: https://clinicaltrials.gov/archive/NCT01779167/2017_05_26, pp. 1-5.

International International Search Report and Written Opinon for PCT/US2017/036016 dated Aug. 28, 2017.

International International Search Report and Written Opinon for PCT/US2017/036005 dated Aug. 29, 2017.

Non-Final Office Action dated Sep. 28, 2017 for U.S. Appl. No. 15/235,720, pp. 9.

Notice of Allowance dated Dec. 27, 2017 for U.S. Appl. No. 14/958,610, pp. 10.

* cited by examiner

|  | VEHICLE | OXYBUTYNIN 10 nM | TOLTERODINE 10 nM | SOLIFENACIN 10 nM |
|---|---|---|---|---|
| CL-316,243 | $E_{max} = 71.0 \pm 3.9\%$<br>$pIC_{50} = 8.0 \pm 0.2$ | $E_{max} = 89.9^* \pm 3.4\%$<br>$pIC_{50} = 8.7^* \pm 0.2$ | $E_{max} = 91.3^* \pm 1.5\%$<br>$pIC_{50} = 8.4 \pm 0.2$ | $E_{max} = 70.9 \pm 1.5\%$<br>$pIC_{50} = 8.1 \pm 0.1$ |
| SOLABEGRON | $E_{max} = 48.3 \pm 3.3\%$<br>$pIC_{50} = 6.8 \pm 0.3$ | $E_{max} = 63.0^* \pm 2.7\%$<br>$pIC_{50} = 7.3^* \pm 0.2$ | $E_{max} = 67.1^* \pm 2.6\%$<br>$pIC_{50} = 7.5^* \pm 0.1$ | $E_{max} = 60.6^* \pm 2.1\%$<br>$pIC_{50} = 7.0 \pm 0.1$ |
| MIRABEGRON | $E_{max} = 71.5 \pm 4.9\%$<br>$pIC_{50} = 5.8 \pm 0.1$ | $E_{max} = 68.2 \pm 2.3\%$<br>$pIC_{50} = 6.1^* \pm 0.1$ | $E_{max} = 81.9^* \pm 3.1\%$<br>$pIC_{50} = 6.5^* \pm 0.2$ | $E_{max} = 68.5^* \pm 3.2\%$<br>$pIC_{50} = 6.1^* \pm 0.1$ |

(*): $p < 0.05$ VERSUS VEHICLE GROUP

FIG. 5

PHARMACEUTICAL COMPOSITIONS AND THE TREATMENT OF OVERACTIVE BLADDER

CROSS-REFERENCE TO RELATED APPLICATIONS

The present application is a Continuation in Part application under 35 U.S.C. § 111(a) of International Application No. PCT/US2015/038583 filed Jun. 30, 2015, which claims priority to U.S. Provisional Application No. 62/020,889 filed Jul. 3, 2014, the disclosures of which are herein incorporated by reference in their entirety.

SUMMARY OF THE INVENTION

Normally, the kidneys produce urine, which drains into the bladder. During urination, urine passes from the bladder through the urethra. As the bladder fills, nerve signals sent to the brain trigger the need to urinate and the nerve signals coordinate the relaxation of the pelvic floor muscles and the muscles of the urethra (urinary sphincter muscles). The muscles of the bladder contract, pushing the urine out (micturition). Overactive bladder occurs because the muscles of the bladder start to contract involuntarily even when the volume of urine in the bladder is low. This involuntary contraction creates the urgent need to urinate.

Overactive bladder (OAB) is a condition characterized by sudden, involuntary contraction of the detrusor muscle of the urinary bladder. This results in a sudden, compelling need to urinate that is difficult to suppress (urinary urgency), even though the bladder may only contain a small amount of urine. The key symptom is the sudden urge to void (urgency) with or without urgency urinary incontinence, often associated with urinary frequency (also known as frequency of mictruitions, voiding 8 or more times per day) and nocturia (awakening one or more times at night to void). Overactive bladder coupled with urinary leakage (inability to suppress the urge to void) is also referred to as urgency urinary incontinence. Approximately 300 mL of urine in the bladder can signal the nerves to trigger muscles of the bladder to coordinate urination. Voluntary control of the sphincter muscles at the opening of the bladder can hold the urine in the bladder for longer. Up to 600 mL of urine can be contained in a normal adult bladder. For those with OAB, the bladder capacity is typically low (<200 mL).

OAB is commonly classified into subtypes including neurogenic, idiopathic, and outlet obstruction. Neurogenic OAB is attributed to coexisting neurological conditions such as Parkinson's disease, multiple sclerosis, spinal cord injury, or stroke. The underlying pathophysiology is the interruption of the otherwise orderly control of micturition, resulting in the symptoms described above. The cause of idiopathic OAB is not as well defined; alterations in signaling within the bladder have been implicated. Finally, OAB may be associated with anatomical changes in the lower urinary tract, for example, in patients with bladder outlet obstruction, which may be the result of an enlarged prostate gland.

Overall, the incidence of OAB increases with age. The ratio of men to women affected depends on the age group, but in general women tend to be more affected than men. OAB represents a significant quality of life burden to patients.

OAB treatment goals include: 1) reduction of urinary urgency and frequency of mictruitions, 2) increase in voided volume (bladder capacity), 3) decrease in urge incontinence (reduction of leakage episodes), and 4) decrease in nocturia.

Physicians and patients remain unsatisfied with the current therapies and desire medicines with improved efficacy and tolerability. In particular, there is an unacceptably high incidence of side effects, including dry mouth and constipation associated with these medications. Also, current medications do not adequately treat urgency, one of the most bothersome symptoms of OAB.

Accordingly, there remains a need for new medicines and methods of treatment that offer improved efficacy and tolerability in the treatment of symptoms associated with overactive bladder, above and beyond the currently available therapies.

The present invention provides pharmaceutical compositions and combinations to treat OAB and the symptoms associated therewith without the unacceptable side effects seen with the current treatment methods. One treatment method according to the present invention comprises treatment with the beta-3 adrenergic receptor agonist solabegron. Another treatment combination according to the invention comprises a beta-3 adrenergic receptor agonist, e.g. solabegron, and a muscarinic receptor antagonist which results in a synergistic effect on the symptoms associated with OAB. The inventors have shown that this combination provides an unexpected increase in bladder capacity measured as voided volume and is therefore useful for the treatment of one or more symptoms associated with OAB. For example, a goal of OAB treatment is to decrease micturition frequency. This is one of the recognized endpoints for treatment of OAB. Accordingly, if voided volume increases, and intake remains the same, then the number of micturitions (i.e. micturition frequency) will decrease. This is a major goal of treating OAB.

Accordingly, in one embodiment, the present application describes a method of treating overactive bladder in a subject in need thereof, comprising administering a therapeutically effective amount of solabegron or a pharmaceutically-acceptable salt, pharmaceutically-acceptable derivative or zwitterion thereof, wherein treating overactive bladder is measured by an increase in voided volume.

In one embodiment the present application describes a method of treating overactive bladder in a subject in need thereof, comprising administering a therapeutically effective amount of solabegron or a pharmaceutically-acceptable salt, pharmaceutically-acceptable derivative, or zwitterion thereof, wherein the voided volume of the subject is increased.

In one embodiment the present application describes a method of treating overactive bladder in a subject in need thereof, comprising administering a combination comprising a therapeutically effective amount of solabegron or a pharmaceutically-acceptable salt, pharmaceutically-acceptable derivative, or zwitterion thereof, and an antimuscarinic receptor agonist or a pharmaceutically-acceptable salt or pharmaceutically-acceptable derivative thereof, wherein treating overactive bladder is measured by an increase in voided volume.

In one embodiment the present application describes a method of treating overactive bladder in a subject in need thereof, comprising administering a combination comprising a therapeutically effective amount of solabegron or a pharmaceutically-acceptable salt, pharmaceutically-acceptable derivative, or zwitterion thereof, and an antimuscarinic receptor agonist or a pharmaceutically-acceptable salt or pharmaceutically-acceptable derivative thereof, wherein the voided volume of the subject is increased.

In one embodiment the present application describes a pharmaceutical composition for treating overactive bladder, comprising solabegron or a pharmaceutically-acceptable salt, pharmaceutically-acceptable derivative, or zwitterion thereof, wherein treating overactive bladder is measured by an increase in voided volume.

In one embodiment the present application describes a pharmaceutical combination for treating overactive bladder comprising, a therapeutically effective amount of solabegron and pharmaceutically-acceptable salts thereof; and a therapeutically effective amount, or a sub-therapeutically effective amount of tolterodine or a pharmaceutically-acceptable salt thereof, wherein treating overactive bladder is measured by an increase in voided volume.

In one embodiment the present application describes a pharmaceutical combination for treating overactive bladder comprising, a therapeutically effective amount of solabegron and pharmaceutically-acceptable salts thereof; and a therapeutically effective amount, or a sub-therapeutically effective amount of oxybutynin or a pharmaceutically-acceptable salt thereof, wherein treating overactive bladder is measured by an increase in voided volume.

In one embodiment the present application describes a pharmaceutical combination for treating overactive bladder comprising, a therapeutically effective amount of solabegron and pharmaceutically-acceptable salts thereof; and a therapeutically effective amount, or a sub-therapeutically effective amount of solifenacin or a pharmaceutically-acceptable salt thereof, wherein treating overactive bladder is measured by an increase in voided volume.

BRIEF DESCRIPTION OF THE DRAWINGS

FIG. 5 shows $E_{max}$ and $pIC_{50}$ values of various beta-3 adrenergeic receptor agonists, either alone (vehicle) or in the presence of 10 nM of various antimuscarinics.

DETAILED DESCRIPTION OF THE INVENTION

Definitions

Figure 1:
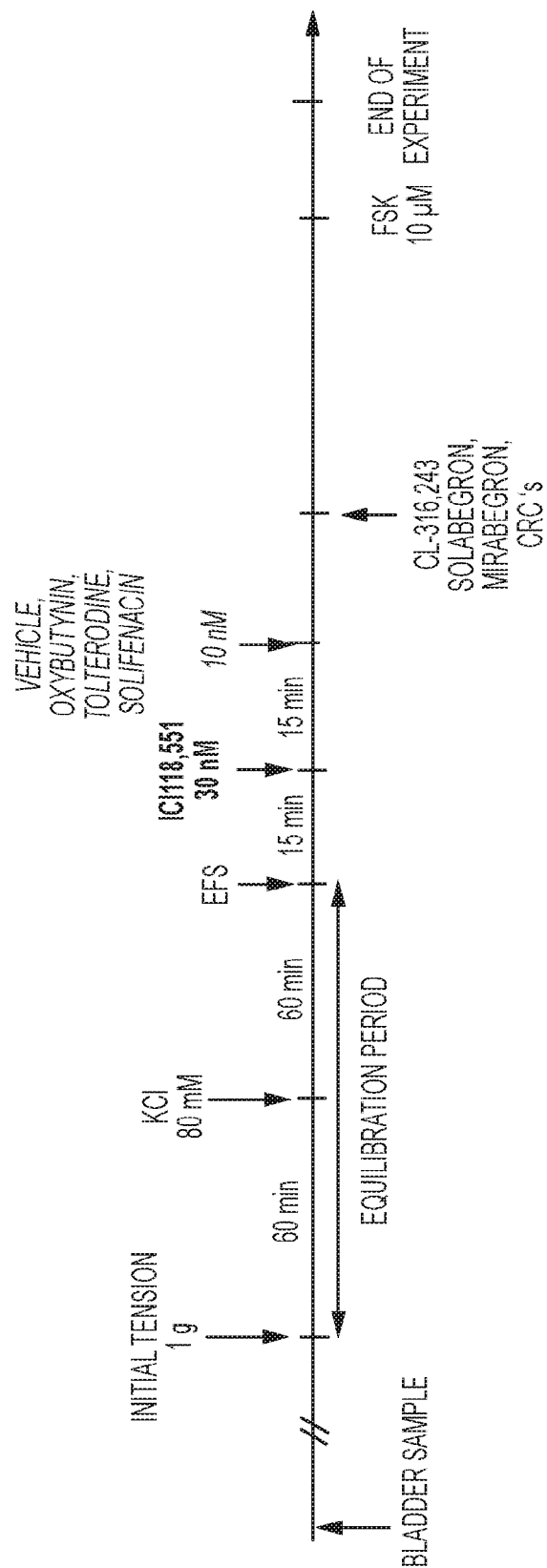
FIG. 1 shows a graph of the Experimental protocol described in Example 3.
Figure 2:
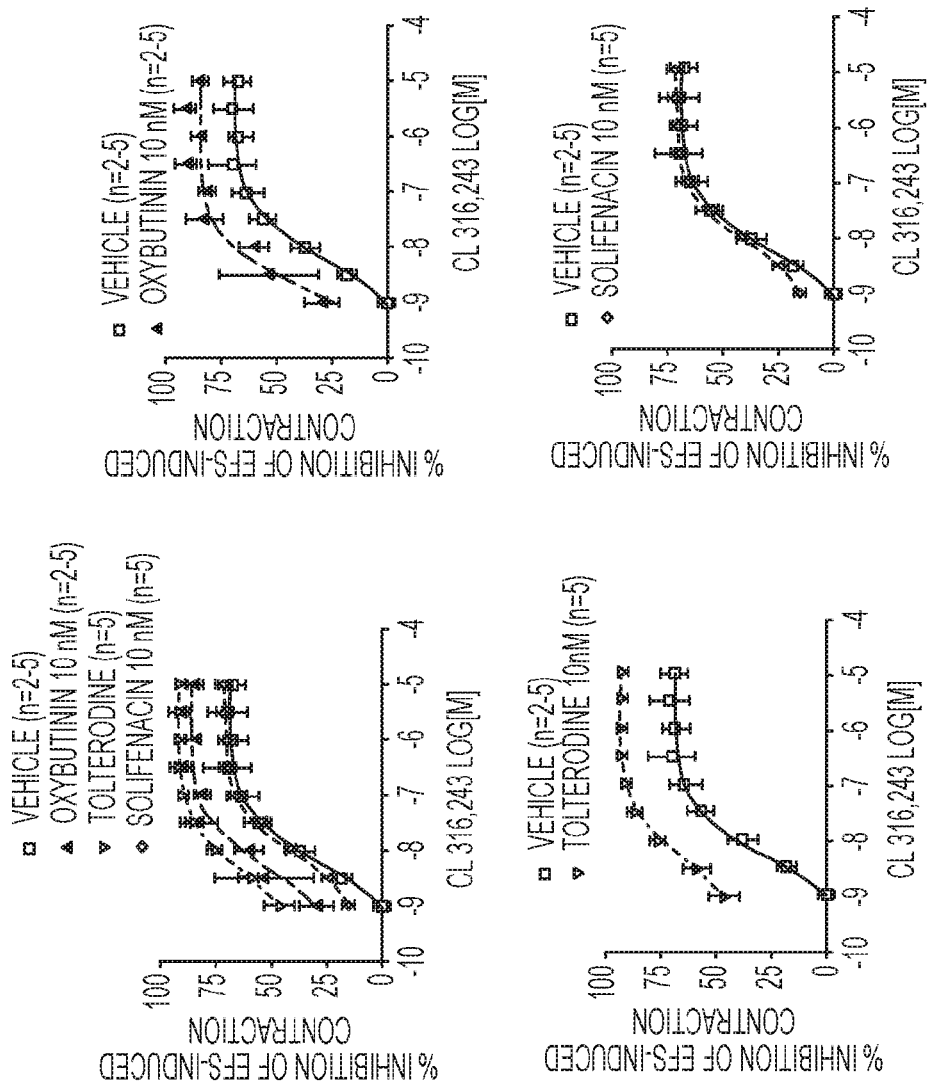
FIG. 2 displays the effects of antimuscarinics on CL-316, 243 inhibition of EFS-induced contractions of rat isolated urinary bladder.
Figure 3:
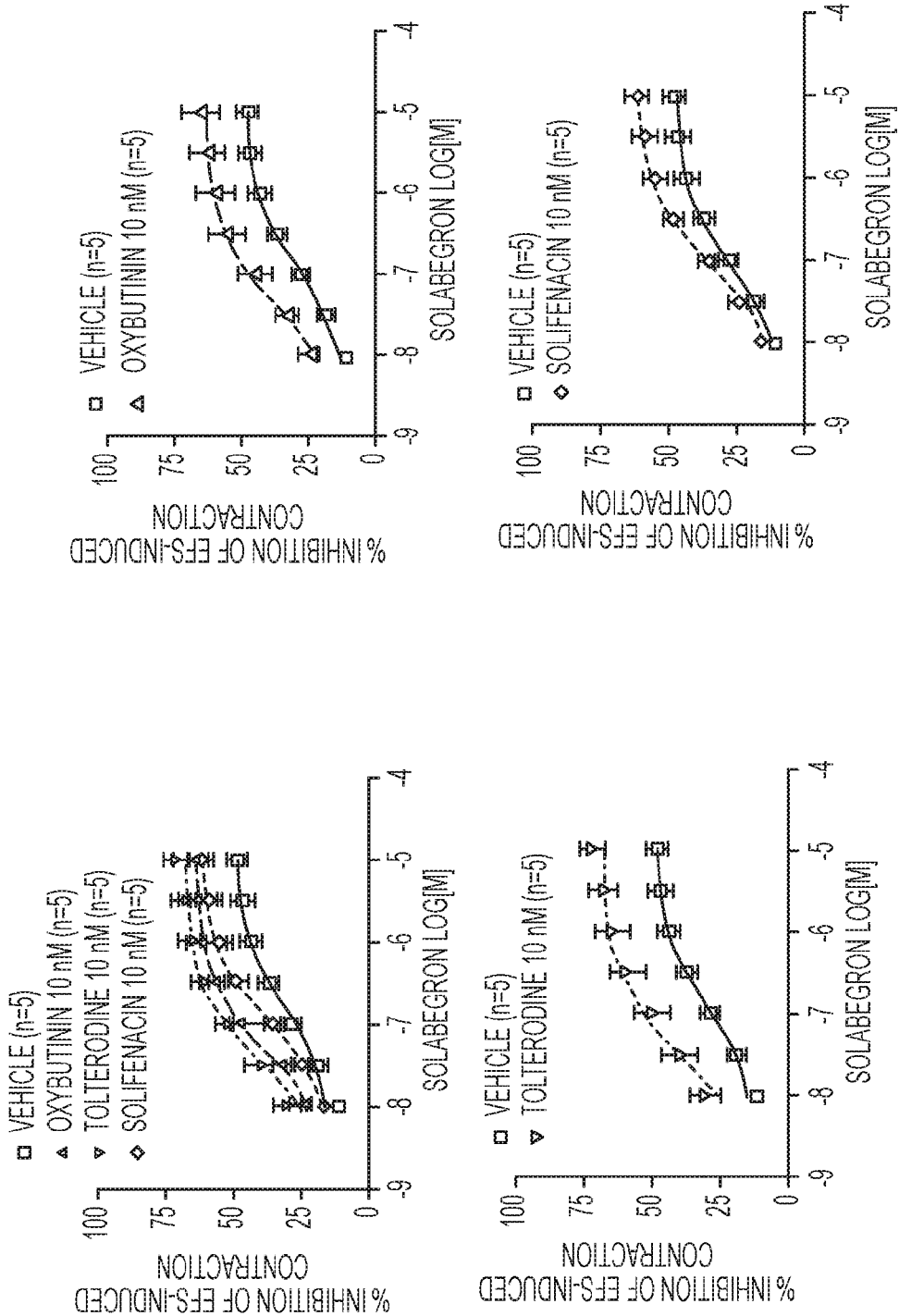
FIG. 3 displays the effects of various antimuscarinics on solabegron inhibition of EFS-induced contractions of rat isolated urinary bladder.
Figure 4:
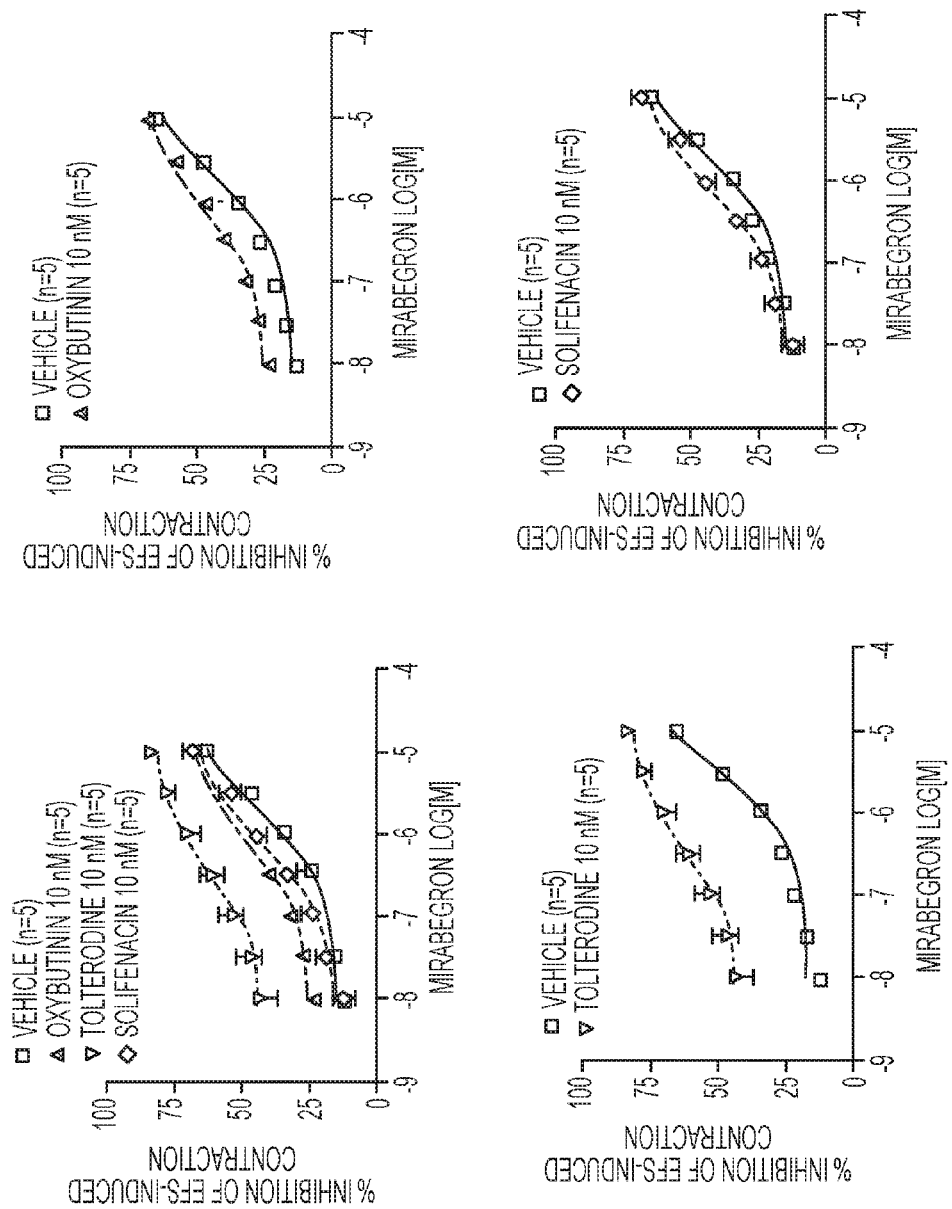
FIG. 4 displays the effects of various antimuscarinics on mirabegron inhibition of EFS-induced contractions of rat isolated urinary bladder.

This invention is not limited to the particular processes, compositions, or methodologies described, as these may vary. The terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "symptom" is a reference to one or more symptoms and equivalents thereof known to those skilled in the art, and so forth.

As used herein, the term "about" means plus or minus 10% of the numerical value of the number with which it is being used. Therefore, about 50 mL means in the range of 45 mL-55 mL.

"Administering" when used in conjunction with a therapeutic means to administer a therapeutic directly into or onto a target tissue or to administer a therapeutic to a patient whereby the therapeutic positively impacts the tissue to which it is targeted. "Administering" a composition may be accomplished orally, by injection, topical administration, or by either method in combination with other known techniques. Such combination techniques include heating, radiation and ultrasound.

The term "animal" as used herein includes, but is not limited to, humans and non-human vertebrates such as wild, domestic and farm animals.

The term "improves" is used to convey that the present invention changes either the appearance, form, characteristics and/or the physical attributes of the tissue to which it is being provided, applied or administered.

The term "inhibiting" includes the administration of a compound of the present invention to prevent the onset of the symptoms, alleviating the symptoms, reducing the symptoms, delaying or decreasing the progression of the disease and/or its symptoms, or eliminating the disease, condition or disorder.

By "pharmaceutically-acceptable" it is meant that the carrier, diluent or excipient must be compatible with the other ingredients of the formulation and not deleterious to the recipient thereof.

The term "pharmaceutically-acceptable derivative," as used herein, refers to pharmaceutically-acceptable solvates, pharmaceutically-acceptable salts solvated with pharmaceutically-acceptable solvents thereof, and metabolites.

As used herein, the term "therapeutic" means an agent utilized to treat, combat, ameliorate, prevent, or improve an unwanted condition or disease of a patient. In part, embodiments of the present invention are directed to the treatment of overactive bladder.

As used herein, the term "effective amount" means the amount of a drug or pharmaceutical agent, or the amount of a combination of drugs or pharmaceutical agents that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder, as was known in the art as of the date of the present invention. The term also includes within its scope amounts effective to enhance normal physiological function, as was known in the art as of the date of the present invention.

Accordingly, the term "sub-therapeutically effective amount" indicates any amount of the muscarinic receptor antagonist which is not therapeutically effective or is minimally therapeutically effective alone, as was known in the art as of the date of the present invention, but which in combination with a therapeutically effective amount of the beta-3 adrenergic receptor agonist, e.g. solabegron, demonstrates a synergistic therapeutic effect. In particular embodiments of the presently claimed combinations and methods, a lower dose (sub-therapeutic dose) of the antimuscarinic agent can be used to produce superior efficacy of the combination due to the synergy of the two compounds, while avoiding or minimizing the side effects of the antimuscarinic agent.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

In some embodiments, the compounds and methods disclosed herein can be utilized with or on a subject in need of such treatment, which can also be referred to as "in need thereof." As used herein, the phrase "in need thereof" means that the subject has been identified as having a need for the particular method or treatment and that the treatment has been given to the subject for that particular purpose.

Generally speaking, the term "tissue" refers to any aggregation of similarly specialized cells which are united in the performance of a particular function.

As used herein, the terms "synergy" and "synergistic", or the phrase "in a synergistic manner," refer to the interaction of two or more drugs in vitro or in vivo so that their combined effect when administered together is greater than the sum of the effects observed when each is administered individually.

As used herein, the term "urinary urgency" is considered the hallmark symptom of OAB, and is the sudden, compelling desire to pass urine that is difficult to defer.

As used herein, the term "urinary frequency" or "frequency of micturitions" refers to the number of times a subject voids and is considered abnormal if the person urinates more than eight times in a day. This frequency is usually monitored by having the person record urination episodes in a voiding diary. The number of episodes varies depending on sleep, fluid intake, medications, and up to seven is considered normal if consistent with the other factors.

The term "nocturia," as used herein, is a symptom where the person complains of interrupted sleep because of an urge to void and, similar to the urinary frequency component, is affected by similar lifestyle and medical factors. Individual waking events are not considered abnormal.

As used herein, the term "urgency urinary incontinence" is a form of urinary incontinence characterized by the involuntary loss of urine occurring for no apparent reason while feeling urinary urgency as discussed above. Urgency urinary incontinence can be measured with pad tests, and these are often used for research purposes. The goal in treating urgency urinary incontinence is to reduce the number of leakage episodes.

As used herein, the term "voided volume" is used as a measure of bladder capacity. Anatomically, functional bladder capacity increases with age from childhood [(years of age+2)×30 mL] to adulthood (300-600 mL). A goal when treating OAB is to increase the bladder capacity or voided volume. An increase in voided volume is a good indicator of the efficacy of a therapy. For example, a goal of OAB treatment is to decrease micturition frequency. This is one of the recognized endpoints for treatment of OAB. Accordingly, if voided volume increases, and intake remains the same, then the number of micturitions (i.e. micturition frequency) will decrease.

As used herein, the terms "muscarinic receptor antagonists," "antimuscarinics", "antimuscarinic agent" and "anticholinergics" are synonymous.

The embodiments set forth herein are described in terms of "comprising", however each of the following embodiments may also be described in terms of "consists of" or "consisting of", meaning that the formulation or method includes only the elements, steps, or ingredients specifically recited in the particular claimed embodiment or claim and each of the embodiments may also be described in terms of "consisting essentially of" or "consists essentially of", meaning that the formulation or method includes only the specified materials or steps and those that do not materially affect the basic and novel characteristics of the claimed invention.

Methods of Treatment

Solabegron

The adult urinary bladder has a total volume capacity range between 300 and 600 mL. A component of bladder capacity is the post-void residual (PVR) urine test, which measures the amount of urine left in the bladder after voluntary bladder emptying (urination). The volume of urine voided or voided volume (functional capacity) plus the PVR volume equals the total bladder capacity.

Total bladder capacity (volume) is also measured clinically in an awake patient by transabdominal ultrasound when the bladder is filled to completion. Total bladder capacity (volume) is calculated by measuring the voided volume by the patient, and then measuring the post-void residual volume by either transabdominal ultrasound or direct measurement by bladder catheterization. Residual urine is defined as the amount left post-voiding and the voided volume is the amount of volume passed during a micturition. Thus, the total bladder capacity (bladder volume) is equal to the voided volume (functional bladder capacity) plus the PVR volume.

Various embodiments of the present invention describe treating overactive bladder in a subject in need thereof, wherein treating overactive bladder is measured by an increase in voided volume.

In some embodiments, the method comprises administering a therapeutically effective amount of solabegron or a pharmaceutically-acceptable salt, pharmaceutically-acceptable derivative or zwitterion thereof. Solabegron is also known as 3'-[(2-{[(2R)-2-(3-chlorophenyl)-2-hydroxyethyl]amino}ethyl)amino]biphenyl-3-carboxylic acid and is depicted in Formula I:

Formula I

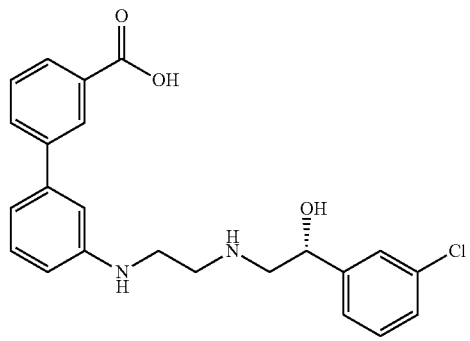

In some embodiments, the solabegron or a pharmaceutically-acceptable salt, pharmaceutically-acceptable derivative or zwitterion thereof, comprises one or more pharmaceutically-acceptable carriers, diluents or excipients.

In some embodiments, solabegron is in the form of the hydrochloride salt (Formula I-HCl). In some embodiments, solabegron is a zwitterion (Formula I-ZW).

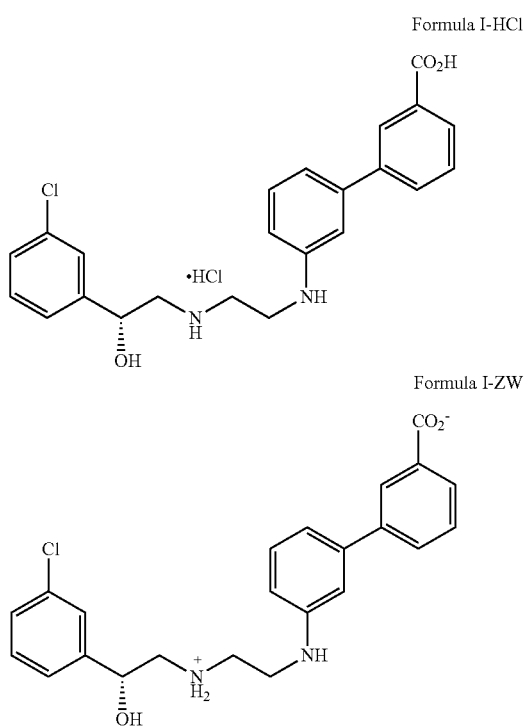

In some embodiments the method of treatment is directed to a method comprising the solabegron or a pharmaceutically-acceptable salt, pharmaceutically-acceptable derivative or zwitterion thereof, further comprising the primary in vivo metabolite of solabegron, Formula (III)

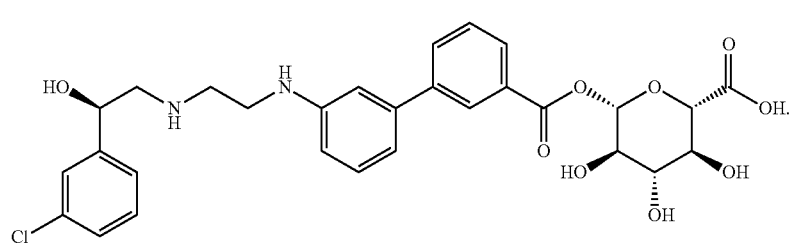

In certain embodiments, the therapeutically effective amount of solabegron or a pharmaceutically-acceptable salt, pharmaceutically-acceptable derivative or zwitterion thereof, may be as a daily dose or a single dose within a range of a lower limit of solabegron and an upper limit amount of solabegron. In some embodiments the lower limit amount of solabegron is about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about, 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, or about 750 mg. In some embodiments, the upper limit amount of solabegron is about 775 mg, about 750 mg, about 725 mg, about 700 mg, about 675 mg, about 650 mg, about 625 mg, about 600 mg, about 575 mg, about 550 mg, about 525 mg, about 500 mg, about 475 mg, about 450 mg, about 425 mg, about 400 mg, about 375 mg, about 350 mg, about 325 mg, about 300 mg, about 275 mg, about 250 mg, about 225 mg, about 200 mg, about 175 mg, about 150 mg, about 125 mg, about 100 mg, about 75 mg, or about 50 mg. In some embodiments, the daily dose may be any range between an upper and a lower limit of ranges previously disclosed.

For example, the daily dose range may be about 25 mg to about 775 mg, about 50 mg to about 500 mg, about 100 mg to about 750 mg, about 150 mg to about 700 mg, about 200 mg to about 400 mg, about 200 mg to about 650 mg, about 250 mg to about 600 mg, about 300 mg to about 550 mg, about 350 mg to about 500 mg, about 400 mg to about 450 mg of solabegron. In some embodiments the daily dose is administered twice daily (i.e. a 25 mg to 775 mg daily dose is administered as two doses of 12.5 mg to 387.5 mg).

In certain embodiments the therapeutically effective amount of solabegron is 50 mg to 500 mg a day given in an immediate release formulation. In certain embodiments the therapeutically effective amount of solabegron is 25 mg to 250 mg, given twice a day in an immediate release formulation. In certain embodiments the therapeutically effective amount is 100 mg to 200 mg, given twice a day in an immediate release formulation.

In certain embodiments the method further comprises, alleviating one or more of the symptoms of overactive bladder selected from the group consisting of urinary urgency, frequency of mictruitions, nocturia, and urgency urinary incontinence, or a combination thereof.

In embodiments described herein, the method of treating overactive bladder in a subject in need thereof, comprises administering a therapeutically effective amount of solabegron or a pharmaceutically-acceptable salt, pharmaceutically-acceptable derivative or zwitterion thereof; wherein treating overactive bladder is measured by an increase in voided volume; and wherein the solabegron is in a pharmaceutical composition comprising one or more pharmaceutically-acceptable carriers, diluents, or excipients.

In embodiments described herein, the method of treating overactive bladder in a subject in need thereof, comprises administering a therapeutically effective amount of a hydrochloride salt of solabegron, wherein treating overactive bladder is measured by an increase in voided volume.

In embodiments described herein, the method of treating overactive bladder in a subject in need thereof, comprises administering a therapeutically effective amount of a zwitterion of solabegron, wherein treating overactive bladder is measured by an increase in voided volume.

In embodiments described herein, the method of treating overactive bladder in a subject in need thereof, comprises administering a therapeutically effective amount of solabegron or a pharmaceutically-acceptable salt, pharmaceutically-acceptable derivative or zwitterion thereof; wherein treating overactive bladder is measured by an increase in voided volume; and wherein the therapeutically effective amount of solabegron is about 25 mg to about 775 mg. In certain embodiments the therapeutically effective amount of solabegron is about 50 mg to about 500 mg, about 100 mg to about 750 mg, about 150 mg to about 700 mg, about 200 mg to about 400 mg, about 200 mg to about 650 mg, about 250 mg to about 600 mg, about 300 mg to about 550 mg, about 350 mg to about 500 mg, about 400 mg to about 450 mg. These dosages may be administered once a day, twice daily, three times a day, or four times a day. In some embodiments the daily dose is administered twice daily (i.e. a 25 mg to 775 mg daily dose is administered as two doses of 12.5 mg to 387.5 mg). In certain embodiments the therapeutically effective amount of solabegron is 50 mg to 500 mg a day given in an immediate release formulation. In certain embodiments the therapeutically effective amount of solabegron is 25 mg to 250 mg, given twice a day in an immediate release formulation. In certain embodiments the therapeutically effective amount is 100 mg to 200 mg, given twice a day in an immediate release formulation.

In embodiments described herein, a method of treating overactive bladder in a subject in need thereof, comprises administering a therapeutically effective amount of solabegron or a pharmaceutically-acceptable salt, pharmaceutically-acceptable derivative or zwitterion thereof; wherein treating overactive bladder is measured by an increase in voided volume and one or more of the symptoms of overactive bladder is alleviated; wherein the one or more symptoms of overactive bladder is selected from the group consisting of urinary urgency, frequency of mictruitions, nocturia, and urgency urinary incontinence, or a combination thereof.

In certain embodiments, a method of treating overactive bladder in a subject in need thereof, comprises administering a therapeutically effective amount of solabegron or a pharmaceutically-acceptable salt, pharmaceutically-acceptable derivative, or zwitterion thereof; wherein the voided volume of the subject is increased.

In embodiments described herein, the method of treating overactive bladder in a subject in need thereof, comprises administering a therapeutically effective amount of solabegron or a pharmaceutically-acceptable salt, pharmaceutically-acceptable derivative or zwitterion thereof; wherein the voided volume of the subject is increased; and wherein the solabegron or a pharmaceutically-acceptable salt, pharmaceutically-acceptable derivative, or zwitterion thereof, is in a pharmaceutical composition comprising one or more pharmaceutically-acceptable carriers, diluents, or excipients.

In embodiments described herein, the method of treating overactive bladder in a subject in need thereof, comprises administering a therapeutically effective amount of a hydrochloride salt of solabegron, wherein the voided volume of the subject is increased.

In embodiments described herein, the method of treating overactive bladder in a subject in need thereof, comprises administering a therapeutically effective amount of a zwitterion of solabegron, wherein the voided volume of the subject is increased.

In embodiments described herein, the method of treating overactive bladder in a subject in need thereof, comprises administering a therapeutically effective amount of solabegron or a pharmaceutically-acceptable salt, pharmaceutically-acceptable derivative or zwitterion thereof, wherein the voided volume of the subject is increased and, wherein the therapeutically effective amount of solabegron is about 25 mg to about 775 mg. In certain embodiments the therapeutically effective amount of solabegron is about 50 mg to about 500 mg, about 100 mg to about 750 mg, about 150 mg to about 700 mg, about 200 mg to about 400 mg, about 200 mg to about 650 mg, about 250 mg to about 600 mg, about 300 mg to about 550 mg, about 350 mg to about 500 mg, about 400 mg to about 450 mg. These dosages may be administered once a day, twice daily, three times a day, or four times a day. In some embodiments the daily dose is administered twice daily (i.e. a 25 mg to 775 mg daily dose is administered as two doses of 12.5 mg to 387.5 mg). In certain embodiments the therapeutically effective amount of solabegron is 50 mg to 500 mg a day given in an immediate release formulation. In certain embodiments the therapeutically effective amount of solabegron is 25 mg to 250 mg, given twice a day in an immediate release formulation. In certain embodiments the therapeutically effective amount is 100 mg to 200 mg, given twice a day in an immediate release formulation. In embodiments described herein, the method of treating overactive bladder in a subject in need thereof, comprises administering a therapeutically effective amount of solabegron or a pharmaceutically-acceptable salt, pharmaceutically-acceptable derivative, or zwitterion thereof, wherein the voided volume of the subject is increased, and one or more of the symptoms of overactive bladder is alleviated, wherein the one or more symptoms of overactive bladder is selected from the group consisting of urinary urgency, frequency of mictruitions, nocturia, and urgency urinary incontinence, or a combination thereof.

Solabegron and a Muscarinic Receptor Antagonist

Unexpectedly, new synergistic drug combinations have also been discovered which are useful in treating one or more symptoms associated with OAB. These combinations comprise solabegron, and a muscarinic receptor antagonist. It has been demonstrated that these combinations have surprisingly increased potency and efficacy, and are useful for the treatment of at least one symptom associated with OAB.

Treating patients with the combination of solabegron and an antimuscarinic agent has now been found to synergistically increase voided volume, thereby increasing total bladder capacity. The combination of solabegron and an antimuscarinic agent, two distinct pharmacological agents modulating independent bladder signaling pathways, produces synergistic increases in bladder capacity, which correlates with clinical improvement.

The bladder receives motor innervation from both sympathetic and parasympathetic nerve fibers. Bladder function is the product of the coordination of two different components of smooth muscles in the bladder, including the detrusor muscle. One component involves parasympathetic nerves responsible for contraction of smooth bladder muscles as the volume of urine stretches the bladder, and the other involves sympathetic nerves that maintain the smooth bladder muscles in a relaxed state despite the stretching of the bladder.

Muscarinic receptor antagonists act via blockade of parasympathetic nerve mediated bladder contraction, while beta-3 adrenergic receptor agonists, e.g. solabegron, exert their effect by binding to beta-3 adrenergic receptors, resulting in relaxation of sympathetic nerve mediated smooth bladder muscle.

Testing of combination of solabegron and a muscarinic receptor antagonist according to the present invention produced a unexpected synergistic increase in voided volume compared to either solabegron or the muscarinic receptor antagonist used alone and is therefore useful for the treatment of one or more symptoms associated with OAB (vide supra).

There was no reason to expect the two neural networks to function complementarily in the bladder, so that blocking muscarinic receptors and activating beta-3 adrenergic receptors would produce even a completely additive increase in bladder capacity and voided volume compared to individual results obtained, let alone a synergistic increase. It was possible that relaxing the bladder muscle provided little further contribution to bladder capacity than already obtained by blocking bladder muscle contraction or vice versa. Accordingly, it was completely unexpected that a synergistic, i.e., more than additive, increase in bladder capacity was obtained by the combination products of the present invention compared to either component used alone when there was no expectation that simultaneous blocking of parasympathetic nerve function and activation of sympathetic function would produce even a fully additive effect.

Muscarinic receptors responding to the natural ligand acetylcholine (ACh) have a widespread tissue distribution and are involved in the control of numerous central and peripheral physiological responses, as well as being a major drug target in human disease. This family of G-protein coupled receptors consists of five members designated M1, M2, M3, M4 and M5. The gene family as a whole shows 26.3% overall amino acid identity, with the variation between the receptor subtypes being seen largely within the intracellular loops. These receptors are sub-divided into two broad groups based on their primary coupling efficiency to G-proteins. Hence, M2 and M4-muscarinic receptors are able to couple to the pertussis-toxin sensitive Gl/o-proteins, and M1, M3 and M5-muscarinic receptors couple to Gq/11-proteins. It is, however, readily apparent that the muscarinic receptor family can couple to a wide range of diverse signaling pathways, some of which are mediated by G-proteins and others that are G-protein-independent.

The role of muscarinic receptors in the direct contraction of smooth muscle, particularly of bladder, ileum, iris and airways, are considered a classical muscarinic response mediated principally by M3-muscarinic receptors expressed on the smooth muscle cells. Co-expressed with the M3-muscarinic receptors in smooth muscle is an often-larger population of M2-muscarinic receptors that appear to play a much lesser role in the smooth muscle contractile response. Exocrine secretion, particularly of saliva, is primarily mediated by M3-muscarinic receptors with a lesser role played by M1-receptors particularly in salvation.

The orthosteric binding pocket of the muscarinic receptor family is highly conserved. (Leach, K., et al., *Handb Exp Pharmacol.* 208:29-48, 2012). Currently, oxybutynin, tolterodine, solifenacin are the leading antimuscarinic drugs that are employed for the treatment of overactive bladder. Tolterodine does not discriminate between the five subtypes. Oxybutynin and solifenacin possess very marginal selectivity (~10-fold) for $M_3$ over the $M_2/M_5$ subtypes, but do not distinguish between $M_3$ and $M_1/M_4$ subtypes Although not wishing to be bound by any particular theory, it is believed that beta-3 adrenergic receptor agonist, e.g. solabegron, exert an effect by binding to beta-3 adrenergic receptors, resulting in relaxation of bladder smooth muscle. It is believed that muscarinic receptor antagonists, such as oxybutynin, act via blockade of parasympathetic nerve mediated bladder contraction. That drugs affecting these two different mechanisms of action provide a synergistic effect that was heretofore both unknown and unexpected.

Accordingly, in some embodiments, the present application describes a method of treating overactive bladder in a subject in need thereof, comprising administering a combination comprising a therapeutically effective amount of solabegron or a pharmaceutically-acceptable salt, pharmaceutically-acceptable derivative, or zwitterion thereof, and a therapeutically or sub-therapeutically effective amount of a muscarinic receptor antagonist or a pharmaceutically-acceptable salt or pharmaceutically-acceptable derivative thereof, wherein treating overactive bladder is measured by an increase in voided volume.

In some embodiments the solabegron or a pharmaceutically-acceptable salt, pharmaceutically-acceptable derivative or zwitterion thereof, is in a pharmaceutical composition comprising one or more pharmaceutically-acceptable carriers, diluents or excipients.

In some embodiments the muscarinic receptor antagonist or a pharmaceutically-acceptable salt or pharmaceutically-acceptable derivative thereof is in a pharmaceutical composition comprising one or more pharmaceutically-acceptable carriers, diluents, or excipients.

In some embodiments, solabegron is in the form of the hydrochloride salt (Formula I-HCl). In some embodiments, solabegron is a zwitterion (Formula I-ZW).

In some embodiments, the muscarinic receptor antagonist is selected from oxybutynin, tolterodine, trospium, darifenacin, festerodine, hyoscyamine, propiverine, or solifenacin, or a pharmaceutically-acceptable salt or pharmaceutically-acceptable derivative thereof. In some embodiments the muscarinic receptor antagonist is selected from oxybutynin, tolterodine, or solifenacin, or a pharmaceutically-acceptable salt or pharmaceutically-acceptable derivative thereof. In some embodiments, muscarinic receptor antagonist is oxybutynin, or a pharmaceutically-acceptable salt or pharmaceutically-acceptable derivative thereof.

Oxybutynin (Formula (II)) has the chemical name 4-diethylaminobut-2-ynyl 2-cyclohexyl-2-hydroxy-2-phenylethanoate also known as 4-(diethylamino)-2-butynyl-α-cyclohexyl-α-hydroxybenzeneacetate, also known as 4-(diethylamino)-2-butyn-1-yl-cyclo-hexyl-(hydroxy)phenylacetate, and may be prepared, for example, according to the procedures provided in UK Patent Specification No. GB940,540, filed Jul. 25, 1961, and published on Oct. 30, 1963. The (S) enantiomer of oxybutynin may be prepared according to the procedures in EP 0806948 B1. The (R)-enantiomer of oxybutynin may be prepared according to the procedures in U.S. Pat. No. 6,123,961. Oxybutynin has been proven to be safe and effective in treating patients with overactive bladder and is marketed globally, although side effects are known.

Formula II

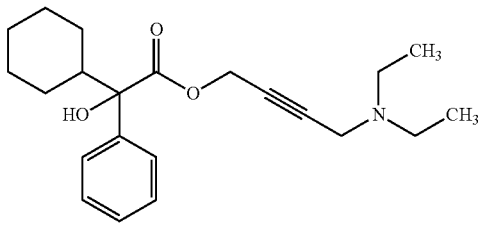

In certain embodiments, the therapeutically effective amount of solabegron or a pharmaceutically-acceptable salt, pharmaceutically-acceptable derivative or zwitterion thereof, may be as a daily dose or a single dose within a range of a lower limit of solabegron and an upper limit amount of solabegron. In some embodiments the lower limit amount of solabegron is about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about, 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, or about 750 mg. In some embodiments, the upper limit amount of solabegron is about 775 mg, about 750 mg, about 725 mg, about 700 mg, about 675 mg, about 650 mg, about 625 mg, about 600 mg, about 575 mg, about 550 mg, about 525 mg, about 500 mg, about 475 mg, about 450 mg, about 425 mg, about 400 mg, about 375 mg, about 350 mg, about 325 mg, about 300 mg, about 275 mg, about 250 mg, about 225 mg, about 200 mg, about 175 mg, about 150 mg, about 125 mg, about 100 mg, about 75 mg, or about 50 mg. In some embodiments, the daily dose may be any range between an upper and a lower limit of ranges previously disclosed.

For example, the daily dose range may be about 25 mg to about 775 mg, about 25 mg to about 500 mg, about 100 mg to about 750 mg, about 150 mg to about 700 mg, about 200 mg to about 400 mg, about 200 mg to about 650 mg, about 250 mg to about 600 mg, about 300 mg to about 550 mg, about 350 mg to about 500 mg, about 400 mg to about 450 mg of solabegron. In some embodiments the daily dose is administered twice daily (i.e. a 25 mg to 775 mg daily dose is administered as two doses of 12.5 mg to 387.5 mg).

In certain embodiments the therapeutically effective amount of solabegron is 25 mg to 500 mg a day given in an immediate release formulation. In certain embodiments the therapeutically effective amount of solabegron is 12.5 mg to 250 mg, given twice a day in an immediate release formulation.

In certain embodiments, the therapeutically effective amount of the muscarinic receptor antagonist is the therapeutically effective amount, as was known in the art as of the date of the present invention.

In one embodiment, a therapeutically effective amount of oxybutynin is, but is not limited to, about 5 mg to about 30 mg daily. In some embodiments, the therapeutically effective amount of oxybutynin is 5 mg two to four times a day in an immediate release formulation. In certain embodiments, the therapeutically effective amount of oxybutynin is about 5 mg, about 10 mg, about 15 mg, about 20 mg, about 25 mg or about 30 mg once a day in an extended release formulation.

In one embodiment, a therapeutically effective amount of tolterodine is, but is not limited to, about 1 mg to about 4 mg daily. In some embodiments, the therapeutically effective amount of tolterodine is about 1 mg to about 2 mg two times a day in an immediate release formulation. In some embodiments, the therapeutically effective amount of tolterodine is about 2 mg to about 4 mg once a day in an extended release formulation.

In one embodiment, a therapeutically effective amount of trospium is, but is not limited to, about 20 mg to about 60 mg daily. In some embodiments, the therapeutically effective amount of trospium is about 20 mg two times a day in an immediate release formulation. In some embodiments, the therapeutically effective amount of trospium is about 60 mg once a day in an extended release formulation.

In one embodiment, a therapeutically effective amount of darifenacin is, but is not limited to, about 7.5 mg to about 15 mg daily. In some embodiments, the therapeutically effective amount of darifenacin is about 7.5 mg to about 15 mg once a day In one embodiment, a therapeutically effective amount of festerodine is, but is not limited to, about 4 mg to about 8 mg daily. In some embodiments, the therapeutically effective amount of festerodine is 4 mg to 8 mg once a day.

In one embodiment, a therapeutically effective amount of hyoscyamine is, but is not limited to, about 0.375 mg to about 0.75 mg daily.

In one embodiment, a therapeutically effective amount of propiverine is, but is not limited to, about 15 mg to about 45 mg daily of propiverine hydrochloride. In some embodiments, the therapeutically effective amount of propiverine is about 15 mg two to three times a day of propiverine hydrochloride.

In one embodiment, a therapeutically effective amount of solifenacin is, but is not limited to, about 5 mg to about 10 mg daily. In some embodiments, the therapeutically effective amount of solifenacin is about 5 mg or about 10 mg once a day.

In certain embodiments, the therapeutically effective amount of the muscarinic receptor antagonist or a pharmaceutically-acceptable salt, or pharmaceutically-acceptable derivative thereof, may be as a daily dose or a single dose within a range of a lower limit of muscarinic receptor antagonist or a pharmaceutically-acceptable salt, or pharmaceutically-acceptable derivative thereof, and an upper limit amount of muscarinic receptor antagonist or a pharmaceutically-acceptable salt, or pharmaceutically-acceptable derivative thereof. In some embodiments the lower limit amount of the muscarinic receptor antagonist is about 0.3 mg, about 0.75 mg, about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, or about 85 mg. In some embodiments, the upper limit amount of the muscarinic receptor antagonist is about 90 mg, about 85 mg, about 80 mg, about 75 mg, about 70 mg, about 65 mg, about 60 mg, about 55 mg, about 50 mg, about 45 mg, about 40 mg, about 35 mg, about 30 mg, about 25 mg, about 20 mg, about 15 mg, about 10 mg, about 5 mg, about 1 mg, or about 0.75 mg. In some embodiments, the daily dose may be any range between an upper and a lower limit of ranges previously disclosed.

For example, the range may be about 0.375 mg to about 0.75 mg, about 1 mg to about 4 mg, about 4 mg to about 8 mg, about 5 mg to about 10 mg, about 5 mg to about 30 mg, about 5 mg to about 85 mg, about 10 mg to about 80 mg, about 15 mg to about 45 mg, about 15 mg to about 75 mg, about 20 mg to about 60 mg, about 20 mg to about 70 mg, about 25 mg to about 65 mg, about 30 mg to about 60 mg, about 35 mg to about 55 mg, about 40 mg to about 50 mg of muscarinic receptor. These dosages may be administered once a day, twice daily, three times a day, or four times a day.

In certain embodiments the sub-therapeutically effective of the muscarinic receptor antagonist is any amount of the muscarinic receptor antagonist which is not therapeutically effective or is minimally therapeutically effective alone, as was known in the art as of the date of the present invention, but which in combination with a therapeutically effective amount of solabegron, demonstrates a synergistic therapeutic effect.

In some embodiments of the invention, the sub-therapeutically effective amount of the muscarinic receptor antagonist or a pharmaceutically-acceptable salt, or pharmaceutically-acceptable derivative thereof, may be as a daily dose or a single dose within a range of a lower limit of the sub-therapeutically effective amount of muscarinic receptor antagonist or a pharmaceutically-acceptable salt, or pharmaceutically-acceptable derivative thereof and an upper limit amount of the sub-therapeutically effective amount of muscarinic receptor antagonist or a pharmaceutically-acceptable salt, or pharmaceutically-acceptable derivative thereof. In some embodiments the lower limit amount of the sub-therapeutically effective amount of the muscarinic receptor antagonist is about 0.1 mg, about 0.5 mg, about 1 mg, about 5 mg, about 10 mg, about 15 mg, about 20 mg, about 25 mg, about 30 mg, about 35 mg, about 40 mg, or about 45 mg. In some embodiments, the upper limit amount of the sub-therapeutically effective amount of the muscarinic receptor antagonist is about 50 mg, about 45 mg, about 40 mg, about 35 mg, about 30 mg, about 25 mg, about 20 mg, about 15 mg, about 10 mg, about 5 mg, or about 1 mg. In some embodiments, the daily dose may be any range between an upper and a lower limit of ranges previously disclosed.

For example, the range may be about 0.1 mg to about 50 mg, about 1 mg to about 45 mg, about 5 mg to about 40 mg, about 10 mg to about 35 mg, about 15 mg to about 30 mg, about 20 mg to about 25 mg, of the sub-therapeutically effective amount of muscarinic receptor antagonist. These dosages may be administered once a day, twice daily, three times a day, or four times a day.

In certain embodiments, the solabegron or a pharmaceutically-acceptable salt, pharmaceutically-acceptable derivative or zwitterion thereof, and the muscarinic receptor antagonist or a pharmaceutically-acceptable salt, or pharmaceutically-acceptable derivative thereof. are co-administered. In some embodiments the solabegron or a pharmaceutically-acceptable salt, pharmaceutically-acceptable derivative or zwitterion thereof, and the muscarinic receptor antagonist or a pharmaceutically-acceptable salt, or pharmaceutically-acceptable derivative thereof, are contained in a single dosage form, wherein the single dosage form is a pharmaceutical composition.

In certain embodiments the solabegron or a pharmaceutically-acceptable salt, pharmaceutically-acceptable derivative or zwitterion thereof, and the muscarinic receptor antagonist or a pharmaceutically-acceptable salt, or pharmaceutically-acceptable derivative thereof, are administered separately.

In some embodiments there is a time delay between the administration of the solabegron or a pharmaceutically-acceptable salt, pharmaceutically-acceptable derivative or zwitterion thereof and the muscarinic receptor antagonist or a pharmaceutically-acceptable salt, pharmaceutically-acceptable derivative or zwitterion thereof. In some embodiments, the time delay between the administration of solabegron or a pharmaceutically-acceptable salt, pharmaceutically-acceptable derivative or zwitterion thereof, and the muscarinic receptor antagonist or a pharmaceutically-acceptable salt, pharmaceutically-acceptable derivative or zwitterion thereof, is 5 minutes, 10 minutes, 15 minutes, 20 minutes, 25 minutes, 30 minutes, 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours or 12 hours.

In some embodiments, the method further comprises alleviating one or more of the symptoms of overactive bladder selected from the group consisting of urinary urgency, frequency of mictruitions, nocturia, and urgency urinary incontinence, or a combination thereof.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative, or zwitterion thereof, and one or more pharmaceutically-acceptable carriers, diluents, or excipients; and a therapeutically effective amount, or a sub-therapeutically effective amount, of a muscarinic receptor antagonist or a pharmaceutically-acceptable salt, or pharmaceutically-acceptable derivative thereof; wherein treating overactive bladder is measured by an increase in voided volume.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative, or zwitterion thereof; and a therapeutically effective amount, or a sub-therapeutically effective amount, of a muscarinic receptor antagonist or a pharmaceutically-acceptable salt, or pharmaceutically-acceptable derivative thereof, and one or more pharmaceutically-acceptable carriers, diluents, or excipients; wherein treating overactive bladder is measured by an increase in voided volume.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative, or zwitterion thereof; and a therapeutically effective amount, or a sub-therapeutically effective amount, of a muscarinic receptor antagonist or a pharmaceutically-acceptable salt, or pharmaceutically-acceptable derivative thereof, selected from a group consisting of oxybutynin, tolterodine, and solifenacin; wherein treating overactive bladder is measured by an increase in voided volume.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative, or zwitterion thereof; and a therapeutically effective amount, or a sub-therapeutically effective amount, of oxybutynin or a pharmaceutically-acceptable salt, or pharmaceutically-acceptable derivative thereof; wherein treating overactive bladder is measured by an increase in voided volume.

In embodiments described herein, the method of treating overactive bladder in a subject in need thereof, comprises administering a combination comprising a therapeutically effective amount of a hydrochloride salt of solabegron; and a therapeutically effective amount, or a sub-therapeutically effective amount, of a muscarinic receptor antagonist or a pharmaceutically-acceptable salt, or pharmaceutically-acceptable derivative thereof; wherein treating overactive bladder is measured by an increase in voided volume.

In embodiments described herein, the method of treating overactive bladder in a subject in need thereof, comprises administering a combination comprising a therapeutically effective amount of a zwitterion of solabegron; and a therapeutically effective amount, or a sub-therapeutically effective amount, of a muscarinic receptor antagonist or a pharmaceutically-acceptable salt, or pharmaceutically-acceptable derivative thereof; wherein treating overactive bladder is measured by an increase in voided volume.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative or zwitterion thereof, and a therapeutically effective amount, or a sub-therapeutically effective amount, of a muscarinic receptor antagonist or a pharmaceutically-acceptable salt, or pharmaceutically-acceptable derivative thereof; wherein treating overactive bladder is measured by an increase in voided volume; and wherein the therapeutically effective amount of solabegron is about 25 mg to about 775 mg. In certain embodiments, the therapeutically effective amount of solabegron is about 25 mg to about 500 mg, about 100 mg to about 750 mg, about 150 mg to about 700 mg, about 200 mg to about 400 mg, about 200 mg to about 650 mg, about 250 mg to about 600 mg, about 300 mg to about 550 mg, about 350 mg to about 500 mg, about 400 mg to about 450 mg. These dosages may be administered once a day, twice daily, three times a day, or four times a day. In some embodiments the daily dose is administered twice daily (i.e. a 25 mg to 775 mg daily dose is administered as two doses of 12.5 mg to 387.5 mg). In certain embodiments the therapeutically effective amount of solabegron is 25 mg to 500 mg a day given in an immediate release formulation. In certain embodiments the therapeutically effective amount of solabegron is 12.5 mg to 250 mg, given twice a day in an immediate release formulation.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative or zwitterion thereof, and a therapeutically effective amount of a muscarinic receptor antagonist or a pharmaceutically-acceptable salt, or pharmaceutically-acceptable derivative thereof; wherein treating overactive bladder is measured by an increase in voided volume; and wherein the therapeutically effective amount of muscarinic receptor antagonist is about 0.3 mg to about 90 mg. In certain embodiments, the therapeutically effective amount of the muscarinic receptor antagonist is about 0.375 mg to about 0.75 mg, about 1 mg to about 4 mg, about 4 mg to about 8 mg, about 5 mg to about 10 mg, about 5 mg to about 30 mg, about 5 mg to about 85 mg, about 10 mg to about 80 mg, about 15 mg to about 45 mg, about 15 mg to about 75 mg, about 20 mg to about 60 mg, about 20 mg to about 70 mg, about 25 mg to about 65 mg, about 30 mg to about 60 mg, about 35 mg to about 55 mg, about 40 mg to about 50 mg. These dosages may be administered once a day, twice daily, three times a day, or four times a day.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative or zwitterion thereof; and a sub-therapeutically effective amount, of a muscarinic receptor antagonist or a pharmaceutically-acceptable salt, or pharmaceutically-acceptable derivative thereof; wherein treating overactive bladder is measured by an increase in voided volume, and wherein the sub-therapeutically effective amount of muscarinic receptor antagonist is any amount of the muscarinic receptor antagonist which is not therapeutically effective or is minimally therapeutically effective alone, as was known in the art as of the date of the present invention, but which in combination with a therapeutically effective amount of solabegron, demonstrates a synergistic therapeutic effect.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative or zwitterion thereof; and a therapeutically effective amount, or a sub-therapeutically effective amount, of muscarinic receptor antagonist or a pharmaceutically-acceptable salt, or pharmaceutically-acceptable derivative thereof; wherein treating overactive bladder is measured by an increase in voided volume, and wherein the solabegron and the muscarinic receptor antagonist are co-administered.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative or zwitterion thereof; and a therapeutically effective amount, or a sub-therapeutically effective amount, of a muscarinic receptor antagonist or a pharmaceutically-acceptable salt, or pharmaceutically-acceptable derivative thereof; wherein treating overactive bladder is measured by an increase in voided volume, and wherein the solabegron and the muscarinic receptor antagonist are contained in a single dosage form, wherein the single dosage form is a pharmaceutical composition.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative or zwitterion thereof; and a therapeutically effective amount, or a sub-therapeutically effective amount, of a muscarinic receptor antagonist or a pharmaceutically-acceptable salt, or pharmaceutically-acceptable derivative thereof; wherein treating overactive bladder is measured by an increase in voided volume, and wherein the solabegron and the muscarinic receptor antagonist are administered separately.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative or zwitterion thereof; and a therapeutically effective amount, or a sub-therapeutically effective amount, of a muscarinic receptor antagonist or a pharmaceutically-acceptable salt, or pharmaceutically-acceptable derivative thereof; wherein treating overactive bladder is measured by an increase in voided volume, and wherein there is a time delay between the administration of the solabegron and the muscarinic receptor antagonist.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative, or zwitterion thereof; and a therapeutically effective amount, or a sub-therapeutically effective amount, of a muscarinic receptor antagonist or a pharmaceutically-acceptable salt, or pharmaceutically-acceptable derivative thereof; wherein treating overactive bladder is measured by an increase in voided volume and one or more of the symptoms of overactive bladder is alleviated; wherein the one or more symptoms of overactive bladder is selected from the group consisting of urinary urgency, frequency of mictruitions, nocturia, and urgency urinary incontinence, or a combination thereof.

In certain embodiments, a method of treating overactive bladder in a subject in need thereof, comprises administering a combination comprising a therapeutically effective amount of solabegron or a pharmaceutically-acceptable salt, pharmaceutically-acceptable derivative, or zwitterion thereof; and a therapeutically effective amount, or a sub-therapeutically effective amount, of a muscarinic receptor antagonist or a pharmaceutically-acceptable salt, or pharmaceutically-acceptable derivative thereof; wherein the voided volume of the subject is increased.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative, or zwitterion thereof; and one or more pharmaceutically-acceptable carriers, diluents, or excipients; and a therapeutically effective amount, or a sub-therapeutically effective amount, of a muscarinic receptor antagonist or a pharmaceutically-acceptable salt, or pharmaceutically-acceptable derivative thereof; wherein the voided volume of the subject is increased.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative, or zwitterion thereof; and a therapeutically effective amount, or a sub-therapeutically effective amount, of a muscarinic receptor antagonist or a pharmaceutically-acceptable salt, or pharmaceutically-acceptable derivative thereof; and one or more pharmaceutically-acceptable carriers, diluents, or excipients; wherein the voided volume of the subject is increased.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative, or zwitterion thereof; and a therapeutically effective amount, or a sub-therapeutically effective amount, of a muscarinic receptor antagonist or a pharmaceutically-acceptable salt, or pharmaceutically-acceptable derivative thereof; selected from a group consisting of oxybutynin, tolterodine, and solifenacin; wherein the voided volume of the subject is increased.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative, or zwitterion thereof; and a therapeutically effective amount, or a sub-therapeutically effective amount, of oxybutynin or a pharmaceutically-acceptable salt, or pharmaceutically-acceptable derivative thereof; wherein the voided volume of the subject is increased.

In embodiments described herein, the method of treating overactive bladder in a subject in need thereof, comprises administering a combination comprising a therapeutically effective amount of a hydrochloride salt of solabegron; and a therapeutically effective amount, or a sub-therapeutically effective amount, of a muscarinic receptor antagonist or a pharmaceutically-acceptable salt, or pharmaceutically-acceptable derivative thereof; wherein the voided volume of the subject is increased.

In embodiments described herein, the method of treating overactive bladder in a subject in need thereof, comprises administering a combination comprising a therapeutically effective amount of a zwitterion of solabegron; and a therapeutically effective amount, or a sub-therapeutically effective amount, of a muscarinic receptor antagonist or a pharmaceutically-acceptable salt, or pharmaceutically-acceptable derivative thereof; wherein the voided volume of the subject is increased.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative or zwitterion thereof; and a therapeutically effective amount, or a sub-therapeutically effective amount, of a muscarinic receptor antagonist or a pharmaceutically-acceptable salt, or pharmaceutically-acceptable derivative thereof; wherein the voided volume of the subject is increased, and wherein the therapeutically effective amount of solabegron is about 25 mg to about 775 mg. In certain embodiments, the therapeutically effective amount of solabegron is about 25 mg to about 500 mg, about 100 mg to about 750 mg, about 150 mg to about 700 mg, about 200 mg to about 400 mg, about 200 mg to about 650 mg, about 250 mg to about 600 mg, about 300 mg to about 550 mg, about 350 mg to about 500 mg, about 400 mg to about 450 mg. These dosages may be administered once a day, twice daily, three times a day, or four times a day. In some embodiments the daily dose is administered twice daily (i.e. a 25 mg to 775 mg daily dose is administered as two doses of 12.5 mg to 387.5 mg). In certain embodiments the therapeutically effective amount of solabegron is 25 mg to 500 mg a day given in an immediate release formulation. In certain embodiments the therapeutically effective amount of solabegron is 12.5 mg to 250 mg, given twice a day in an immediate release formulation.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative or zwitterion thereof; and a therapeutically effective amount, or a sub-therapeutically effective amount, of a muscarinic receptor antagonist or a pharmaceutically-acceptable salt, or pharmaceutically-acceptable derivative thereof; wherein the voided volume of the subject is increased, and wherein the therapeutically effective amount of muscarinic receptor antagonist or a pharmaceutically-acceptable salt, or pharmaceutically-acceptable derivative thereof, is about 0.3 mg to about 90 mg. In certain embodiments, the therapeutically effective amount of the muscarinic receptor antagonist is about 0.375 mg to about 0.75 mg, about 1 mg to about 4 mg, about 4 mg to about 8 mg, about 5 mg to about 10 mg, about 5 mg to about 30 mg, about 5 mg to about 85 mg, about 10 mg to about 80 mg, about 15 mg to about 45 mg, about 15 mg to about 75 mg, about 20 mg to about 60 mg, about 20 mg to about 70 mg, about 25 mg to about 65 mg, about 30 mg to about 60 mg, about 35 mg to about 55 mg, about 40 mg to about 50 mg. These dosages may be administered once a day, twice daily, three times a day, or four times a day.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative or zwitterion thereof; and a therapeutically effective amount, or a sub-therapeutically effective amount, of a muscarinic receptor antagonist or a pharmaceutically-acceptable salt, or pharmaceutically-acceptable derivative thereof; wherein the voided volume of the subject is increased, and wherein the sub-therapeutically effective amount of muscarinic receptor antagonist or a pharmaceutically-acceptable salt, or pharmaceutically-acceptable derivative thereof, is any amount of the muscarinic receptor antagonist which is not therapeutically effective or is minimally therapeutically effective alone, as was known in the art as of the date of the present invention, but which in combination with a therapeutically effective amount of solabegron, demonstrates a synergistic therapeutic effect.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative or zwitterion thereof; and a therapeutically effective amount of a muscarinic receptor antagonist or a pharmaceutically-acceptable salt, or pharmaceutically-acceptable derivative thereof; wherein the voided volume of the subject is increased, and wherein the therapeutically effective amount of solabegron or a pharmaceutically-acceptable salt, pharmaceutically-acceptable derivative or zwitterion thereof, is about 25 mg to about 775 mg and wherein the therapeutically effective amount of muscarinic receptor antagonist or a pharmaceutically-acceptable salt, or pharmaceutically-acceptable derivative thereof, is about 0.3 mg to about 90 mg. In certain embodiments, the therapeutically effective amount of solabegron is about 25 mg to about 500 mg, about 100 mg to about 750 mg, about 150 mg to about 700 mg, about 200 mg to about 400 mg, about 200 mg to about 650 mg, about 250 mg to about 600 mg, about 300 mg to about 550 mg, about 350 mg to about 500 mg, about 400 mg to about 450 mg. These dosages may be administered once a day, twice daily, three times a day, or four times a day. In some embodiments the daily dose is administered twice daily (i.e. a 25 mg to 775 mg daily dose is administered as two doses of 12.5 mg to 387.5 mg). In certain embodiments the therapeutically effective amount of solabegron is 25 mg to 500 mg a day given in an immediate release formulation. In certain embodiments the therapeutically effective amount of solabegron is 12.5 mg to 250 mg, given twice a day in an immediate release formulation. In certain embodiments, the therapeutically effective amount of the muscarinic receptor antagonist is about 0.375 mg to about 0.75 mg, about 1 mg to about 4 mg, about 4 mg to about 8 mg, about 5 mg to about 10 mg, about 5 mg to about 30 mg, about 5 mg to about 85 mg, about 10 mg to about 80 mg, about 15 mg to about 45 mg, about 15 mg to about 75 mg, about 20 mg to about 60 mg, about 20 mg to about 70 mg, about 25 mg to about 65 mg, about 30 mg to about 60 mg, about 35 mg to about 55 mg, about 40 mg to about 50 mg. These dosages may be administered once a day, twice daily, three times a day, or four times a day.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative or zwitterion thereof; and a sub-therapeutically effective amount, of a muscarinic receptor antagonist or a pharmaceutically-acceptable salt, or pharmaceutically-acceptable derivative thereof; wherein the voided volume of the subject is increased; and wherein the therapeutically effective amount of solabegron about 25 mg to about 775 mg, and wherein the sub-therapeutically effective amount of muscarinic receptor antagonist or a pharmaceutically-acceptable salt, or pharmaceutically-acceptable derivative thereof; is any amount of the muscarinic receptor antagonist which is not therapeutically effective or is minimally therapeutically effective alone, as was known in the art as of the date of the present invention, but which in combination with a therapeutically effective amount of solabegron, demonstrates a synergistic therapeutic effect. In certain embodiments, the therapeutically effective amount of solabegron is about 25 mg to about 500 mg, about 100 mg to about 750 mg, about 150 mg to about 700 mg, about 200 mg to about 400 mg, about 200 mg to about 650 mg, about 250 mg to about 600 mg, about 300 mg to about 550 mg, about 350 mg to about 500 mg, about 400 mg to about 450 mg. These dosages may be administered once a day, twice daily, three times a day, or four times a day. In some embodiments the daily dose is administered twice daily (i.e. a 25 mg to 775 mg daily dose is administered as two doses of 12.5 mg to 387.5 mg). In certain embodiments the therapeutically effective amount of solabegron is 25 mg to 500 mg a day given in an immediate release formulation. In certain embodiments the therapeutically effective amount of solabegron is 12.5 mg to 250 mg, given twice a day in an immediate release formulation.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative or zwitterion thereof; and a therapeutically effective amount, or a sub-therapeutically effective amount, of a muscarinic receptor antagonist or a pharmaceutically-acceptable salt, or pharmaceutically-acceptable derivative thereof; wherein the voided volume of the subject is increased, and wherein the solabegron and the muscarinic receptor antagonist are co-administered.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative or zwitterion thereof; and a therapeutically effective amount, or a sub-therapeutically effective amount, of a muscarinic receptor antagonist or a pharmaceutically-acceptable salt or pharmaceutically-acceptable derivative thereof; wherein the voided volume of the subject is increased, and wherein the solabegron and the muscarinic receptor antagonist are contained in a single dosage form, wherein the single dosage form is a pharmaceutical composition.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative or zwitterion thereof; and a therapeutically effective amount, or a sub-therapeutically effective amount, of a muscarinic receptor antagonist or a pharmaceutically-acceptable salt or pharmaceutically-acceptable derivative thereof; wherein the voided volume of the subject is increased, and wherein the solabegron and the muscarinic receptor antagonist are administered separately.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative or zwitterion thereof; and a therapeutically effective amount, or a sub-therapeutically effective amount, of a muscarinic receptor antagonist or a pharmaceutically-acceptable salt or pharmaceutically-acceptable derivative thereof; wherein the voided volume of the subject is increased, and wherein there is a time delay between the administration of the solabegron and the muscarinic receptor antagonist.

In embodiments described herein, the method of treating overactive bladder in a subject in need thereof, comprises administering a combination comprising a therapeutically effective amount of solabegron or a pharmaceutically-acceptable salt, pharmaceutically-acceptable derivative, or zwitterion thereof; and a therapeutically effective amount, or a sub-therapeutically effective amount, of a muscarinic receptor antagonist or a pharmaceutically-acceptable salt or pharmaceutically-acceptable derivative thereof; wherein the voided volume of the subject is increased and one or more of the symptoms of overactive bladder is alleviated; wherein the one or more symptoms of overactive bladder is selected from the group consisting of urinary urgency, frequency of mictruitions, nocturia, and urgency urinary incontinence, or a combination thereof.

The methods of the present invention may also be employed with other therapeutic methods of treating one or more symptoms associated with overactive bladder. Combination therapies according to the present invention thus include the administration of the beta-3 adrenergic receptor agonist, e.g. solabegron, and the muscarinic receptor antagonist as well as optional use of other therapeutic agents including other beta-3 adrenergic receptor agonists and/or muscarinic receptor antagonists. Such combination of agents may be administered together or separately and, when administered separately this may occur simultaneously or sequentially in any order, both close and remote in time. The amounts of the compounds of the beta-3 adrenergic receptor agonist and the muscarinic receptor antagonist and the other optional pharmaceutically active agent(s) and the relative timings of administration will be selected in order to achieve the desired combined therapeutic effect.

Pharmaceutical Compositions
Solabegron

In some embodiments, a pharmaceutical composition for treating overactive bladder comprises solabegron or a pharmaceutically-acceptable salt, pharmaceutically-acceptable derivative, or zwitterion thereof; and one or more pharmaceutically-acceptable carriers, diluents, or excipients; wherein treating overactive bladder is measured by an increase in voided volume.

In some embodiments the solabegron (Formula I) of the composition can be administered as a salt, which can be anhydrous, hydrated, or solvated with a pharmaceutically-acceptable solvent such as ethanol. In a particular embodiment, solabegron is administered as the hydrochloride salt (Formula I-HCl). In a preferred embodiment, solabegron hydrochloride is the anhydrous hydrochloride salt.

The free base, and pharmaceutically-acceptable salts, for example, the hydrochloride salt, of solabegron can be prepared, for example, according to the procedures disclosed in International Patent Application No. PCT/EP99/03958, filed Jun. 9, 1999, and published as WO 99/65877 on Dec. 23, 1999; International Patent Application No. PCT/GB00/04697, filed Dec. 8, 2000 and published as WO 01/42195 on Jun. 14, 2001; and International Patent Application No. PCT/US01/49355, filed Dec. 17, 2001 and published as WO2006/113649 on Aug. 29, 2002.

In some embodiments, the solabegron of the composition can be administered as a zwitterion (Formula I-ZW). In certain embodiments, the solabegron zwitterion in the composition is a solid. In some embodiments, the solabegron zwitterion is amorphous. In further embodiments, the solabegron zwitterion in the composition is a crystal. In some embodiments, the solabegron zwitterion in the composition is a single polymorph. In further embodiments, the solabegron zwitterion in the composition is more than one polymorph. In further embodiments, the solabegron zwitterion in the composition is a solid or crystalline hydrate of isopropanol solvate. In some embodiments, the solabegron zwitterion in the composition is characterized by a peak at 1552 cm−1 upon infrared analysis. In further embodiments, the solabegron zwitterion in the composition is characterized by a peak at 184.6° C. upon differential scanning calorimetry analysis. In some embodiments, the solabegron zwitterion in the composition is characterized by an x-ray powder diffraction pattern having peaks expressed in degrees 2θ (±2) at 6.3, 12.6; 18.6; 18.9; 20.9; 22.4; 25.3; and 25.5. In some embodiments, the solabegron zwitterion in the composition is characterized by an x-ray powder diffraction pattern having peaks expressed in degrees 2θ (±2) at 6.2, 12.5; 18.8; 20.6; and 25.2. In some embodiments, the solabegron zwitterion in the composition is characterized by an x-ray powder diffraction pattern having peaks expressed in degrees 2θ (±2) at 6.2, 12.5; 18.6; 18.8; 20.6; 22.3, and 25.2. In some embodiments, the solabegron zwitterion in the composition is characterized by an x-ray powder diffraction pattern having peaks expressed in degrees 2θ (±2) at 6.2, 12.5; 16.9, 18.6; 18.8; 20.6; 21.1, 21.5; 22.3, 25.2; 26.6, and 32.9. In some embodiments, the solabegron zwitterion in the composition is characterized by an x-ray powder diffraction pattern having peaks expressed in degrees 2θ (±2) at 17.6, 18.7, 19.6, 20.1, 20.5, 23.7, and 25.8. In some embodiments, the solabegron zwitterion in the composition is characterized by an x-ray powder diffraction pattern having peaks expressed in degrees 2θ (±2) at 9.4, 15.1, 16.2, 17.6, 18.7, 19.6, 20.1, 20.5, 21.8, 22.6, 23.7, 24.8, 25.8, and 28.9. In some embodiments, the solabegron zwitterion in the composition is characterized by an x-ray powder diffraction pattern having peaks expressed in degrees 2θ (±2) at 6.1, 7.5, 9.4, 11.3, 14.5, 15.1, 16.2, 17.6, 18.7, 19.6, 20.1, 20.5, 21.8, 22.6, 23.7, 24.8, 25.8, and 28.9. In further embodiments, the solabegron zwitterion in the composition is characterized by $^1$H NMR peaks ($^1$H NMR, 300 MHz, DMSO-d$_6$) δ 8.15; 7.90; 7.70; 7.40; 7.30; 7.19; 6.82; 6.63; 6.00; 4.83; 3.30; 2.95; and 2.82. In some embodiments, the solabegron zwitterion in the composition is characterized by $^{13}$C NMR of the peak ($^{13}$NMR, 300 MHz, DMSO-d$_6$) δ 170.0; 148.0; 145.5; 140.3; 140.1; 135.4; 133.9; 130.0; 129.6; 129.0; 128.3; 128.0; 127.3; 127.1; 125.7; 124.5; 114.8; 111.8; 110.7; 62.8; 54.8; 44.6; 40.8; 40.0; 39.8; 39.4; 39.2; 38.8; 38.6; and 25.4. In further embodiments, the solabegron zwitterion in the composition is at least about 98.0% by weight pure. In some embodiments, the solabegron zwitterion in the composition is at least about 98.0% by weight pure. In some embodiments, the solabegron zwitterion in the composition is at least about 99.0% by weight pure. In further embodiments, the solabegron zwitterion in the composition is at least about 99.5% by weigh pure. In some embodiments, solabegron zwitterion in the composition is at least about 99.9% by weight pure. In further embodiments, the compound of solabegron zwitterion in the composition has no single impurity present in an amount greater than about 0.5% by weight. In some embodiments, the solabegron zwitterion in the composition has no single impurity present in an amount greater than about 0.25% by weight. In further embodiments, the solabegron zwitterion in the composition has no single impurity present in an amount greater than about 0.10% by weight.

In certain embodiments, the therapeutically effective amount of solabegron or a pharmaceutically-acceptable salt, pharmaceutically-acceptable derivative or zwitterion thereof, may be as a daily dose or a single dose within a range of a lower limit of solabegron or a pharmaceutically-acceptable salt, pharmaceutically-acceptable derivative or zwitterion thereof and an upper limit amount of solabegron or a pharmaceutically-acceptable salt, pharmaceutically-acceptable derivative or zwitterion thereof. In some embodiments the lower limit amount of solabegron is about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about, 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, or about 750 mg. In some embodiments, the upper limit amount of solabegron is about 775 mg, about 750 mg, about 725 mg, about 700 mg, about 675 mg, about 650 mg, about 625 mg, about 600 mg, about 575 mg, about 550 mg, about 525 mg, about 500 mg, about 475 mg, about 450 mg, about 425 mg, about 400 mg, about 375 mg, about 350 mg, about 325 mg, about 300 mg, about 275 mg, about 250 mg, about 225 mg, about 200 mg, about 175 mg, about 150 mg, about 125 mg, about 100 mg, about 75 mg, or about 50 mg. In some embodiments, the daily dose may be any range between an upper and a lower limit of ranges previously disclosed.

For example, the daily dose range may be about 25 mg to about 775 mg, about 50 mg to about 500 mg, about 100 mg to about 750 mg, about 150 mg to about 700 mg, about 200 mg to about 400 mg, about 200 mg to about 650 mg, about 250 mg to about 600 mg, about 300 mg to about 550 mg, about 350 mg to about 500 mg, about 400 mg to about 450 mg of solabegron. In some embodiments the daily dose is administered twice daily (i.e. a 25 mg to 775 mg daily dose is administered as two doses of 12.5 mg to 387.5 mg).

In certain embodiments the therapeutically effective amount of solabegron is 50 mg to 500 mg a day given in an immediate release formulation. In certain embodiments the therapeutically effective amount of solabegron is 25 mg to 250 mg, given twice a day in an immediate release formulation. In certain embodiments the therapeutically effective amount is 100 mg to 200 mg, given twice a day in an immediate release formulation.

In some embodiments, a pharmaceutical composition for treating overactive bladder comprises solabegron or a pharmaceutically-acceptable salt, pharmaceutically-acceptable derivative, or zwitterion thereof; wherein treating overactive bladder is measured by an increase in voided volume; and wherein the pharmaceutically-acceptable salt of the solabegron is the hydrochloride salt.

In some embodiments, a pharmaceutical composition for treating overactive bladder comprises solabegron or a pharmaceutically-acceptable salt, pharmaceutically-acceptable derivative, or zwitterion thereof; wherein treating overactive bladder is measured by an increase in voided volume; and wherein the solabegron is a zwitterion.

In some embodiments, a pharmaceutical composition for treating overactive bladder comprises solabegron or a pharmaceutically-acceptable salt, pharmaceutically-acceptable derivative, or zwitterion thereof; wherein treating overactive bladder is measured by an increase in voided volume; and wherein the therapeutically effective amount of solabegron is about 25 mg to about 775 mg. In certain embodiments the therapeutically effective amount of solabegron is about 50 mg to about 500 mg, about 100 mg to about 750 mg, about 150 mg to about 700 mg, about 200 mg to about 400 mg, about 200 mg to about 650 mg, about 250 mg to about 600 mg, about 300 mg to about 550 mg, about 350 mg to about 500 mg, about 400 mg to about 450 mg. is about 50 mg to about 800 mg. In certain embodiments, the therapeutically effective amount of solabegron or a pharmaceutically-acceptable salt, pharmaceutically-acceptable derivative, or zwitterion thereof, is about 100 mg to about 750 mg, about 150 mg to about 700 mg, about 200 mg to about 650 mg, about 250 mg to about 600 mg, about 300 mg to about 550 mg, about 350 mg to about 500 mg, and about 400 mg to about 450 mg of compound. These dosages may be administered once a day, twice daily, three times a day, or four times a day. In some embodiments the daily dose is administered twice daily (i.e. a 25 mg to 775 mg daily dose is administered as two doses of 12.5 mg to 387.5 mg). In certain embodiments the therapeutically effective amount of solabegron is 50 mg to 500 mg a day given in an immediate release formulation. In certain embodiments the therapeutically effective amount of solabegron is 25 mg to 250 mg, given twice a day in an immediate release formulation. In certain embodiments the therapeutically effective amount is 100 mg to 200 mg, given twice a day in an immediate release formulation.

Solabegron and a Muscarinic Receptor Antagonist

In some embodiments, a pharmaceutical combination for treating overactive bladder comprises a therapeutically effective amount of solabegron, or a pharmaceutically-acceptable salt, pharmaceutically-acceptable derivative, or zwitterion thereof; and a therapeutically effective amount, or a sub-therapeutically effective amount, of a muscarinic receptor antagonist; wherein treating overactive bladder is measured by an increase in voided volume.

In some embodiments the solabegron or a pharmaceutically-acceptable salt, pharmaceutically-acceptable derivative or zwitterion thereof, further comprises one or more pharmaceutically-acceptable carriers, diluents or excipients.

In some embodiments the muscarinic receptor antagonist further comprises one or more pharmaceutically-acceptable carriers, diluents, or excipients.

In some embodiments, solabegron is in the form of the hydrochloride salt (Formula I-HCl). In some embodiments, solabegron is a zwitterion (Formula I-ZW).

In some embodiments, the muscarinic receptor antagonist is selected from oxybutynin, tolterodine, trospium, darifenacin, festerodine, hyoscyamine, propiverine, or solifenacin, or pharmaceutically-acceptable salts thereof. In some embodiments the muscarinic receptor antagonist is selected from oxybutynin, tolterodine, or solifenacin, or pharmaceutically-acceptable salts thereof. In some embodiments, muscarinic receptor antagonist is oxybutynin, or pharmaceutically-acceptable salts thereof.

In certain embodiments, the therapeutically effective amount of solabegron or a pharmaceutically-acceptable salt, pharmaceutically-acceptable derivative or zwitterion thereof, may be as a daily dose or a single dose within a range of a lower limit of solabegron or a pharmaceutically-acceptable salt, pharmaceutically-acceptable derivative or zwitterion thereof and an upper limit amount of solabegron or a pharmaceutically-acceptable salt, pharmaceutically-acceptable derivative or zwitterion thereof. In some embodiments the lower limit amount of solabegron is about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about, 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, or about 750 mg. In some embodiments, the upper limit amount of solabegron is about 775 mg, about 750 mg, about 725 mg, about 700 mg, about 675 mg, about 650 mg, about 625 mg, about 600 mg, about 575 mg, about 550 mg, about 525 mg, about 500 mg, about 475 mg, about 450 mg, about 425 mg, about 400 mg, about 375 mg, about 350 mg, about 325 mg, about 300 mg, about 275 mg, about 250 mg, about 225 mg, about 200 mg, about 175 mg, about 150 mg, about 125 mg, about 100 mg, about 75 mg, or about 50 mg. In some embodiments, the daily dose may be any range between an upper and a lower limit of ranges previously disclosed.

For example, the daily dose range may be about 25 mg to about 775 mg, about 25 mg to about 500 mg, about 100 mg to about 750 mg, about 150 mg to about 700 mg, about 200 mg to about 400 mg, about 200 mg to about 650 mg, about 250 mg to about 600 mg, about 300 mg to about 550 mg, about 350 mg to about 500 mg, about 400 mg to about 450 mg of solabegron. In some embodiments the daily dose is administered twice daily (i.e. a 25 mg to 775 mg daily dose is administered as two doses of 12.5 mg to 387.5 mg).

In certain embodiments the therapeutically effective amount of solabegron is 25 mg to 500 mg a day given in an immediate release formulation. In certain embodiments the therapeutically effective amount of solabegron is 12.5 mg to 250 mg, given twice a day in an immediate release formulation.

In certain embodiments, the therapeutically effective amount of the muscarinic receptor antagonist or a pharmaceutically-acceptable salt, or pharmaceutically-acceptable derivative thereof, may be as a daily dose or a single dose within a range of a lower limit of muscarinic receptor antagonist or a pharmaceutically-acceptable salt, or pharmaceutically-acceptable derivative thereof, and an upper limit amount of muscarinic receptor antagonist or a pharmaceutically-acceptable salt, or pharmaceutically-acceptable derivative thereof. In some embodiments the lower limit amount of the muscarinic receptor antagonist is about 0.3 mg, about 0.75 mg, about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, or about 85 mg. In some embodiments, the upper limit amount of the muscarinic receptor antagonist is about 90 mg, about 85 mg, about 80 mg, about 75 mg, about 70 mg, about 65 mg, about 60 mg, about 55 mg, about 50 mg, about 45 mg, about 40 mg, about 35 mg, about 30 mg, about 25 mg, about 20 mg, about 15 mg, about 10 mg, about 5 mg, about 1 mg, or about 0.75 mg. In some embodiments, the daily dose may be any range between an upper and a lower limit of ranges previously disclosed.

For example, the range may be about 0.375 mg to about 0.75 mg, about 1 mg to about 4 mg, about 4 mg to about 8 mg, about 5 mg to about 10 mg, about 5 mg to about 30 mg, about 5 mg to about 85 mg, about 10 mg to about 80 mg, about 15 mg to about 45 mg, about 15 mg to about 75 mg, about 20 mg to about 60 mg, about 20 mg to about 70 mg, about 25 mg to about 65 mg, about 30 mg to about 60 mg, about 35 mg to about 55 mg, about 40 mg to about 50 mg of muscarinic receptor. These dosages may be administered once a day, twice daily, three times a day, or four times a day.

In certain embodiments, the therapeutically effective amount of the muscarinic receptor antagonist amount is the therapeutically effective amount, as was known in the art as of the date of the present invention.

In one embodiment, a therapeutically effective amount of oxybutynin is, but is not limited to, about 5 mg to about 30 mg daily. In some embodiments, the therapeutically effective amount of oxybutynin is 5 mg two to four times a day in an immediate release formulation. In certain embodiments, the therapeutically effective amount of oxybutynin is about 5 mg, about 10 mg, about 15 mg, about 20 mg, about 25 mg or about 30 mg once a day in an extended release formulation.

In one embodiment, a therapeutically effective amount of tolterodine is, but is not limited to, about 1 mg to about 4 mg daily. In some embodiments, the therapeutically effective amount of tolterodine is about 1 mg to about 2 mg two times a day in an immediate release formulation. In some embodiments, the therapeutically effective amount of tolterodine is about 2 mg to about 4 mg once a day in an extended release formulation.

In one embodiment, a therapeutically effective amount of trospium is, but is not limited to, about 20 mg to about 60 mg daily. In some embodiments, the therapeutically effective amount of trospium is about 20 mg two times a day in an immediate release formulation. In some embodiments, the therapeutically effective amount of trospium is about 60 mg once a day in an extended release formulation.

In one embodiment, a therapeutically effective amount of darifenacin is, but is not limited to, about 7.5 mg to about 15 mg daily. In some embodiments, the therapeutically effective amount of darifenacin is about 7.5 mg to about 15 mg once a day In one embodiment, a therapeutically effective amount of festerodine is, but is not limited to, about 4 mg to about 8 mg daily. In some embodiments, the therapeutically effective amount of festerodine is 4 mg to 8 mg once a day.

In one embodiment, a therapeutically effective amount of hyoscyamine is, but is not limited to, about 0.375 mg to about 0.75 mg daily.

In one embodiment, a therapeutically effective amount of propiverine is, but is not limited to, about 15 mg to about 45 mg daily of propiverine hydrochloride. In some embodiments, the therapeutically effective amount of propiverine is about 15 mg two to three times a day of propiverine hydrochloride.

In one embodiment, a therapeutically effective amount of solifenacin is, but is not limited to, about 5 mg to about 10 mg daily. In some embodiments, the therapeutically effective amount of solifenacin is about 5 mg or about 10 mg once a day.

In certain embodiments the sub-therapeutically effective of the muscarinic receptor antagonist is any amount of the muscarinic receptor antagonist which is not therapeutically effective or is minimally therapeutically effective alone, as was known in the art as of the date of the present invention, but which in combination with a therapeutically effective amount of solabegron, demonstrates a synergistic therapeutic effect.

In some embodiments of the invention, the sub-therapeutically effective amount of the muscarinic receptor antagonist or a pharmaceutically-acceptable salt, or pharmaceutically-acceptable derivative thereof, may be as a daily dose or a single dose within a range of a lower limit of the sub-therapeutically effective amount of muscarinic receptor antagonist or a pharmaceutically-acceptable salt, or pharmaceutically-acceptable derivative thereof and an upper limit amount of the sub-therapeutically effective amount of muscarinic receptor antagonist or a pharmaceutically-acceptable salt, or pharmaceutically-acceptable derivative thereof. In some embodiments the lower limit amount of the sub-therapeutically effective amount of the muscarinic receptor antagonist is about 0.1 mg, about 0.5 mg, about 1 mg, about 5 mg, about 10 mg, about 15 mg, about 20 mg, about 25 mg, about 30 mg, about 35 mg, about 40 mg, or about 45 mg. In some embodiments, the upper limit amount of the sub-therapeutically effective amount of the muscarinic receptor antagonist is about 50 mg, about 45 mg, about 40 mg, about 35 mg, about 30 mg, about 25 mg, about 20 mg, about 15 mg, about 10 mg, about 5 mg, or about 1 mg. In some embodiments, the daily dose may be any range between an upper and a lower limit of ranges previously disclosed.

For example, the range may be about 0.1 mg to about 50 mg, about 1 mg to about 45 mg, about 5 mg to about 40 mg, about 10 mg to about 35 mg, about 15 mg to about 30 mg, about 20 mg to about 25 mg, of the sub-therapeutically effective amount of muscarinic receptor antagonist. These dosages may be administered once a day, twice daily, three times a day, or four times a day.

In some embodiments of the invention, the muscarinic receptor antagonist comprises a compound selected from the group consisting of oxybutynin, tolterodine, and solifenacin, or pharmaceutically-acceptable salts and pharmaceutically-acceptable derivatives thereof. In some embodiments, the muscarinic receptor antagonist comprises oxybutynin, in a total daily oral dose of about 1 mg to about 40 mg, preferably about 1 mg to about 20 mg, more preferably about 2.5 mg to about 10 mg. In some embodiment, oxybutynin is administered in a total daily dose of 3.9 mg in a transdermal patch. In certain embodiments, oxybutynin is administered transdermally as a gel which delivers 84 mg of oxybutynin. In another embodiment, the muscarinic receptor antagonist comprises tolterodine, in a total daily oral dose of about 1 mg to about 10 mg, preferably about 1 mg to about 8 mg, more preferably about 1 mg to about 4 mg. In some embodiments, tolterodine is administered in a total daily dose of 4 mg. In certain embodiments, 2 mg of tolterodine is administered twice a day. In still another embodiment, the muscarinic receptor antagonist comprises solifenacin, in a total daily oral dose of about 1 mg to about 20 mg, preferably about 2.5 mg to about 15 mg, more preferably about 2.5 mg to about 10 mg. In some embodiments, solifenacin is administered in a total daily dose of 5 mg. These drugs may be administered once a day, twice daily, three times a day, or four times a day. In certain embodiments, the solabegron and the muscarinic receptor antagonist are co-administered. In some embodiments the solabegron and the muscarinic receptor antagonist are contained in a single dosage form.

In some embodiments, the pharmaceutical compositions of the present invention are formulated to reduce desensitization of the beta-3 adrenoceptor, particularly when compared to an immediate release formulation of solabegron that may be given, for example, twice daily. To prevent or reduce beta-3 adrenoceptor desensitization, the pharmaceutical compositions of solabegron or the pharmaceutical compositions comprising solabegron and an muscarinic receptor antagonist are formulated so that therapeutic administration occurs in a manner such that drug occupancy at the receptor occurs at levels that do not elicit significant receptor desensitization.

Thus in one embodiment, the present application describes a pharmaceutical composition comprising a therapeutically effective amount of solabegron, wherein the pharmaceutical composition achieves a first target $C_{max}$, a second target $C_{max}$, a first target $C_{min}$ between the first target $C_{max}$ and the second target $C_{max}$, and a second target $C_{min}$ after the second target $C_{max}$. Further embodiments describe pharmaceutical compositions, wherein said pharmaceutical composition achieves a plasma concentration of about 1 µg/ml or less for about 6 hours to about 9 hours during a twenty-four hour period. Further embodiments describe pharmaceutical compositions, wherein said pharmaceutical composition achieves a target AUC of about 11,000 ng·hr/ml to about 30,000 ng·hr/ml over a twenty-four hour period. Further embodiments describe pharmaceutical compositions, wherein the first target $C_{max}$ is achieved after the start of a first release of solabegron and the second target $C_{max}$ is achieved after the start of a second release of solabegron. Further embodiments describe pharmaceutical compositions, wherein said first target $C_{max}$ is about 0.5 µg/ml to about 3.5 µg/ml. Further embodiments describe pharmaceutical compositions, wherein said second target $C_{max}$ is about 1.5 µg·ml to about 4 µg/ml. Further embodiments describe pharmaceutical compositions, wherein said first $C_{min}$ is about 0.25 µg/ml to about 1.5 µg/ml. Further embodiments describe pharmaceutical compositions, wherein said second $C_{min}$ is about 0.01 µg/ml to about 1.0 µg/ml. Further embodiments describe pharmaceutical compositions, wherein the time between the first target $C_{max}$ and the second target $C_{max}$ is about 2 to about 8 hours. Further embodiments describe pharmaceutical compositions, wherein the first $C_{min}$ is achieved at about 4 to about 8 hours after the first administration. Further embodiments describe pharmaceutical compositions, wherein the second $C_{min}$ is achieved before about 24 hours after administration of the pharmaceutical composition. Further embodiments describe pharmaceutical compositions, wherein the first $C_{max}$ is achieved at about 0.75 to about 4 hours after the first administration. Further embodiments describe pharmaceutical compositions, wherein the second $C_{max}$ is achieved at about 2 to about 8 hours after the first $C_{min}$. Further embodiments describe pharmaceutical compositions, wherein the first release comprises about 75 mg to about 400 mg of solabegron. Further embodiments describe pharmaceutical compositions, wherein the second release comprises about 100 mg to about 400 mg of solabegron. Further embodiments describe pharmaceutical compositions, further comprising one or more muscarinic receptor antagonists as described herein.

In certain embodiments, the solabegron or a pharmaceutically-acceptable salt, pharmaceutically-acceptable derivative or zwitterion thereof, and the muscarinic receptor antagonist or a pharmaceutically-acceptable salt, or pharmaceutically-acceptable derivative thereof, are co-administered. In some embodiments the solabegron and the muscarinic receptor antagonist are contained in a single dosage form.

In certain embodiments the solabegron or a pharmaceutically-acceptable salt, pharmaceutically-acceptable derivative or zwitterion thereof, and the muscarinic receptor antagonist or a pharmaceutically-acceptable salt, or pharmaceutically-acceptable derivative thereof, are administered separately. In some embodiments there is a time delay between the administration of the solabegron or a pharmaceutically-acceptable salt, pharmaceutically-acceptable derivative or zwitterion thereof, and the muscarinic receptor antagonist or a pharmaceutically-acceptable salt, or pharmaceutically-acceptable derivative thereof. In some embodiments, the time delay between the administration of the beta-3 adrenergic receptor agonist and the muscarinic receptor antagonist is 5 minutes, 10 minutes, 15 minutes, 20 minutes, 25 minutes, 30 minutes, 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours or 12 hours.

One preferred pharmaceutical composition comprises solabegron, or a pharmaceutically-acceptable salt, pharmaceutically-acceptable derivative or zwitterion thereof, tolterodine, or a pharmaceutically-acceptable salt, or pharmaceutically-acceptable derivative thereof, and one or more pharmaceutically-acceptable carriers, diluents or excipients. Another preferred pharmaceutical composition comprises solabegron, or a pharmaceutically-acceptable salt, pharmaceutically-acceptable derivative or zwitterion thereof, oxybutynin, or a pharmaceutically-acceptable salt, or pharmaceutically-acceptable derivative thereof, and one or more pharmaceutically-acceptable carriers, diluents or excipients. Another preferred pharmaceutical composition comprises solabegron or a pharmaceutically-acceptable salt, pharmaceutically-acceptable derivative or zwitterion thereof, solifenacin, or a pharmaceutically-acceptable salt, or pharmaceutically-acceptable derivative thereof, and one or more pharmaceutically-acceptable carriers, diluents or excipients.

In some embodiments, a pharmaceutical combination for treating overactive bladder comprises a therapeutically effective amount of solabegron, or a pharmaceutically-acceptable salt, pharmaceutically-acceptable derivative, or zwitterion thereof; and a therapeutically effective amount, or a sub-therapeutically effective amount, of a muscarinic receptor antagonist or a pharmaceutically-acceptable salt, or pharmaceutically-acceptable derivative thereof, selected from the group consisting of oxybutynin, tolterodine, trospium, darifenacin, festerodine, hyoscyamine, propiverine, solifenacin, and pharmaceutically-acceptable salts thereof; wherein treating overactive bladder is measured by an increase in voided volume; and wherein the solabegron or a pharmaceutically-acceptable salt, pharmaceutically-acceptable derivative, or zwitterion thereof, further comprises one or more pharmaceutically-acceptable carriers, diluents, or excipients.

In some embodiments, a pharmaceutical combination for treating overactive bladder comprises a therapeutically effective amount of solabegron, or a pharmaceutically-acceptable salt, pharmaceutically-acceptable derivative, or zwitterion thereof; and a therapeutically effective amount, or a sub-therapeutically effective amount, of a muscarinic receptor antagonist or a pharmaceutically-acceptable salt or pharmaceutically-acceptable derivative thereof, selected from the group consisting of oxybutynin, tolterodine, trospium, darifenacin, festerodine, hyoscyamine, propiverine, and solifenacin, or pharmaceutically-acceptable salts or pharmaceutically-acceptable derivative thereof; wherein treating overactive bladder is measured by an increase in voided volume; and wherein the muscarinic receptor antagonist or a pharmaceutically-acceptable salt, or pharmaceutically-acceptable derivative thereof, further comprises one or more pharmaceutically-acceptable carriers, diluents, or excipients.

In some embodiments, a pharmaceutical combination for treating overactive bladder comprises a therapeutically effective amount of solabegron, or a pharmaceutically-acceptable salt, pharmaceutically-acceptable derivative, or zwitterion thereof; and a therapeutically effective amount, or a sub-therapeutically effective amount, of a muscarinic receptor antagonist or a pharmaceutically-acceptable salt or pharmaceutically-acceptable derivative thereof, selected from the group consisting of oxybutynin, tolterodine, trospium, darifenacin, festerodine, hyoscyamine, propiverine, and solifenacin, or a pharmaceutically-acceptable salt or pharmaceutically-acceptable derivative thereof; wherein treating overactive bladder is measured by an increase in voided volume, and wherein the solabegron or a pharmaceutically-acceptable salt, pharmaceutically-acceptable derivative, or zwitterion thereof; and the muscarinic receptor antagonist or a pharmaceutically-acceptable salt, or pharmaceutically-acceptable derivative thereof; further comprises one or more pharmaceutically-acceptable carriers, diluents, or excipients.

In some embodiments, a pharmaceutical combination for treating overactive bladder comprises a therapeutically effective amount of solabegron, or a pharmaceutically-acceptable salt, pharmaceutically-acceptable derivative, or zwitterion thereof; and a therapeutically effective amount, or a sub-therapeutically effective amount, of a muscarinic receptor antagonist or a pharmaceutically-acceptable salt or pharmaceutically-acceptable derivative thereof, selected from the group consisting of oxybutynin, tolterodine, solifenacin, and pharmaceutically-acceptable salts thereof; wherein treating overactive bladder is measured by an increase in voided volume.

In some embodiments, a pharmaceutical combination for treating overactive bladder comprises a therapeutically effective amount of solabegron, or a pharmaceutically-acceptable salt, pharmaceutically-acceptable derivative, or zwitterion thereof; and a therapeutically effective amount, or a sub-therapeutically effective amount, of oxybutynin; or a pharmaceutically-acceptable salt or pharmaceutically-acceptable derivative thereof, wherein treating overactive bladder is measured by an increase in voided volume.

In some embodiments, a pharmaceutical combination for treating overactive bladder comprises a therapeutically effective amount of a hydrochloride salt of solabegron, and a therapeutically effective amount, or a sub-therapeutically effective amount, of a muscarinic receptor antagonist selected from the group consisting of oxybutynin, tolterodine, trospium, darifenacin, festerodine, hyoscyamine, propiverine, solifenacin, and or a pharmaceutically-acceptable salt or pharmaceutically-acceptable derivative thereof; wherein treating overactive bladder is measured by an increase in voided volume.

In some embodiments, a pharmaceutical combination for treating overactive bladder comprises a therapeutically effective amount of a zwitterion of solabegron, and a therapeutically effective amount, or a sub-therapeutically effective amount, of a muscarinic receptor antagonist selected from the group consisting of oxybutynin, tolterodine, trospium, darifenacin, festerodine, hyoscyamine, propiverine, solifenacin, or a pharmaceutically-acceptable salt or pharmaceutically-acceptable derivative thereof, wherein treating overactive bladder is measured by an increase in voided volume.

In some embodiments, a pharmaceutical combination for treating overactive bladder comprises a therapeutically effective amount of solabegron, or a pharmaceutically-acceptable salt, pharmaceutically-acceptable derivative, or zwitterion thereof; and a therapeutically effective amount, or a sub-therapeutically effective amount, of a muscarinic receptor antagonist, selected from the group consisting of oxybutynin, tolterodine, trospium, darifenacin, festerodine, hyoscyamine, propiverine, and solifenacin, or a pharmaceutically-acceptable salt or pharmaceutically-acceptable derivative thereof wherein treating overactive bladder is measured by an increase in voided volume; and wherein the solabegron or a pharmaceutically-acceptable salt, pharmaceutically-acceptable derivative, or zwitterion thereof and the muscarinic receptor antagonist or a pharmaceutically-acceptable salt or pharmaceutically-acceptable derivative thereof, are contained in a single dosage form.

In some embodiments, a pharmaceutical combination for treating overactive bladder comprises a therapeutically effective amount of solabegron, or a pharmaceutically-acceptable salt, pharmaceutically-acceptable derivative, or zwitterion thereof; and a therapeutically effective amount, or a sub-therapeutically effective amount, of a muscarinic receptor antagonist or a pharmaceutically-acceptable salt or pharmaceutically-acceptable derivative thereof selected from the group consisting of oxybutynin, tolterodine, trospium, darifenacin, festerodine, hyoscyamine, propiverine, and solifenacin, or a pharmaceutically-acceptable salt or pharmaceutically-acceptable derivative thereof; wherein treating overactive bladder is measured by an increase in voided volume; and wherein the solabegron or a pharmaceutically-acceptable salt, pharmaceutically-acceptable derivative, or zwitterion thereof and the muscarinic receptor antagonist or a pharmaceutically-acceptable salt or pharmaceutically-acceptable derivative thereof are contained in a separate dosage forms.

While it is possible that, for use in medical therapy, the beta-3 adrenergic receptor agonist, e.g. solabegron, or a pharmaceutically-acceptable salt, pharmaceutically-acceptable derivative, or zwitterion thereof; muscarinic receptor antagonist, or a pharmaceutically-acceptable salt or pharmaceutically-acceptable derivative thereof; may be administered as the chemical compound itself, the active ingredient or ingredients may also be administered formulated as a pharmaceutical composition. Accordingly, the invention further provides pharmaceutical compositions, which include therapeutically effective amounts of the beta-3 adrenergic receptor agonist, solabegron, and therapeutically effective amounts, or sub-therapeutically effective amounts, of the muscarinic receptor antagonist, or pharmaceutically-acceptable salts thereof, and one or more pharmaceutically-acceptable carriers, diluents, or excipients. The carrier(s), diluent(s) or excipient(s) must be acceptable in the sense of being compatible with the other ingredients of the formulation, capable of pharmaceutical formulation, and not deleterious to the recipient thereof. The invention also provides a process for the preparation of a pharmaceutical formulation including admixing the beta-3 adrenergic receptor agonist, solabegron, muscarinic receptor antagonist or pharmaceutically-acceptable salts thereof, with one or more pharmaceutically-acceptable carriers, diluents or excipients.

Pharmaceutical formulations may be presented in unit dose forms containing a predetermined amount of active ingredient per unit dose. As is known to those skilled in the art, the amount of active ingredient per dose will depend on the condition being treated, the route of administration and the age, weight and condition of the patient, or the pharmaceutical formulations may be presented in unit dose forms containing a predetermined amount of active ingredient per unit dose. Preferred unit dosage formulations are those containing a daily dose or sub-dose, or an appropriate fraction thereof, of an active ingredient. Furthermore, such pharmaceutical formulations may be prepared by any of the methods well known in the pharmacy art.

Typically, the salts of the present invention are pharmaceutically-acceptable salts. Salts encompassed within the term "pharmaceutically-acceptable salts" refer to non-toxic salts of the compounds of this invention. Salts of the compounds of the present invention may comprise acid addition salts derived from a nitrogen on a substituent in a compound of the present invention. Representative pharmaceutically-acceptable salts include the following: acetate, acid phosphate, aluminum, amines, amino acids, ascorbate, benzenesulfonate, benzoate, bicarbonate, bisulfate, bitartrate, borate, bromide, calcium edetate, camsylate, carbonate, chloride, clavulanate, chloroprocaine, choline, citrate, N,N'-dibenzylethylenediamine, dicyclohexylamine, diethanolamine, dihydrochloride, edetate, edisylate, estolate, esylate, ethanesulfonate, ethylenediamine, formate, fumarate, gentisinate, glucaronate, gluceptate, gluconate, glutamate, glycollyl-arsanilate, hexyl-resorcinate, hydrabamine, hydrobromide, hydrochloride, hydroiodide, hydroxy-naphthoate, iodide, iron, isethionate, isonicotinate, lactate, lactobionate, laurate, lithium, magnesium, malate, maleate, mandelate, mesylate, methanesulfonate, methylbromide, methylnitrate, methyl sulfate, monopotassium maleate, mucate, napsylate, nitrate, N-methylglucamine, oxalate, pamoate (embonate), palmitate, pantothenate, phosphate/diphosphate, polygalacturonate, potassium, procaine, saccharate, salicylate, sodium, stearate, subacetate, succinate, sulfate, tannate, tartrate, teoclate, p-toluenesulfonate, tosylate, triethiodide, trimethylammonium, valerate, and zinc. Other salts, which are not pharmaceutically-acceptable, may also be useful in the preparation of compounds of the invention and form a further aspect of the invention.

The beta-3 adrenergic receptor agonist, e.g. solabegron or a pharmaceutically-acceptable salt, pharmaceutically-acceptable derivative, or zwitterion thereof, and the muscarinic receptor antagonist or a pharmaceutically-acceptable salt or pharmaceutically-acceptable derivative thereof may be administered by any appropriate route. Suitable routes include oral, rectal, nasal, and parenteral (including intravesical, subcutaneous, intramuscular, intraveneous, transdermal, intradermal, intrathecal, and epidural). Administration can also be by means of a bladder pump or sustained release in the bladder.

It will be appreciated that the preferred route may vary with, for example, the condition of the recipient of the combination. It will also be appreciated that each of the agents administered may be administered by the same or different routes and that the beta-3 adrenergic receptor agonist and muscarinic receptor antagonist may be compounded together in a pharmaceutical composition/formulation.

Further, the combinations and methods of the present invention can comprise isotopes of solabegron and/or the muscarinic receptor antagonist, that is, the beta-3 adrenergic receptor agonists and/or muscarinic receptor antagonists are isotopically labeled. In one embodiment, the isotopically labeled compound has one or more hydrogen atoms replaced with either deuterium or tritium. In another embodiment, the isotopically labeled compound has one or more carbon atoms replaced with $^{11}$C, $^{13}$C or $^{14}$C. In one preferred embodiment the composition comprises deuterated solabegron.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically-acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be used in granulating. The powder mixture can be run through a tablet machine, and if the result is imperfectly formed slugs, they can be broken into granules, and the granules can be lubricated and incorporated back into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example, by coating or embedding particulate material in polymers, waxes or the like.

The agents for use according to the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Agents for use according to the present invention may also be delivered by the use of monoclonal antibodies as individual carriers to which the compound molecules are coupled. The compounds may also be coupled with soluble polymers as targetable drug carriers. Such polymers can include, without limitation, polyvinylpyrrolidone, pyran copolymer, poly-hydroxypropyl-methacrylamide-phenol, polyhydroxyethyl-aspartamide-phenol or poly-ethyleneoxide-polylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for rectal administration may be presented as suppositories or as enemas.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question; for example, those suitable for oral administration may include flavoring agents.

In another embodiment, the pharmaceutical combination includes the beta-3 adrenergic receptor agonist, e.g. solabegron or a pharmaceutically-acceptable salt, pharmaceutically-acceptable derivative, or zwitterion thereof, and the muscarinic receptor antagonist or a pharmaceutically-acceptable salt or pharmaceutically-acceptable derivative thereof and optionally at least one additional beta-3 adrenergic receptor agonist or muscarinic receptor antagonist. The muscarinic receptor antagonist is as described herein above.

Therapeutically effective amounts of the beta-3 adrenergic receptor agonist, solabegron, and therapeutically effective amounts, or sub-therapeutically effective amounts of the muscarinic receptor antagonist, and optionally additional beta-3 adrenergic receptor agonist or muscarinic receptor antagonist are administered to a mammal. Typically, the therapeutically effective amount of one of the administered agents of the present invention will depend upon a number of factors including, for example, the age and weight of the mammal, the precise condition requiring treatment, the severity of the condition, the nature of the formulation, and the route of administration. Ultimately, the therapeutically effective amount will be at the discretion of the attendant physician or veterinarian. Further, a lower dose (sub-therapeutic dose) of the antimuscarinic agent can be administered to provide superior efficacy of the combination while controlling the side effects of the antimuscarinic agent.

The invention encompasses the treatment of any condition that is susceptible to agonism of the beta-3 adrenergic receptor, or antagonism of the muscarinic receptor, or a condition that is susceptible to both agonism of the beta-3 adrenergic receptor, and antagonism of the muscarinic receptor.

Examples of conditions associated with over-activity of smooth muscle which are suitable for treatment using a combination comprising the beta-3 adrenergic receptor agonist and the muscarinic receptor antagonist of the present invention include OAB, gastrointestinal syndromes such as irritable bowel syndrome (IBS), inflammatory bowel disease (IBD), ulcerative colitis, and the like. The pharmaceutical combination of the present invention may therefore be effective in the treatment of such conditions. Beta-3 adrenergic receptors have also been found in cardiac tissue. The pharmaceutical combination of the present invention may therefore be effective in the treatment of cardiovascular disease.

The following examples are intended to be illustrative of particular embodiments of the invention, and are not intended to limit the scope of the invention in any way.

EXAMPLES

As used herein the symbols and conventions used in these processes, schemes and examples are consistent with those used in the contemporary scientific literature, for example, the *Journal of the American Chemical Society and the Journal of Biological Chemistry*. Unless otherwise noted, all starting materials were obtained from commercial suppliers and used without further purification. Specifically, the following abbreviations may be used in the examples and throughout the specification:

| BID | twice daily |
| ECG | Electrocardiogram |
| g (grams) | mg (milligrams) |
| IR | immediate release |
| L (liters) | mL (milliliters) |
| µL (microliters) | mol (moles) |
| M (molar) | mM (millimolar) |
| N (Normal) | Kg (kilogram) |
| mmol (millimoles) | RT (room temperature) |
| min (minutes) | h (hours) |
| QID | four times daily |
| XL | extended release |

Example 1. Drug Interaction Study with Healthy Human Subjects

A drug interaction study was conducted in healthy human volunteers, using repeat oral doses of solabegron and oxybutynin administered singly as well as in combination with each other, in order to assess the effects on pharmacokinetic and pharmacodynamic parameters, as measured by post void residual (PVR) volumes. PVR was measured in subjects treated with each agent alone as well as in combination at steady-state.

The study was a two-cohort randomized, open label, repeat dose, 3-way crossover study in healthy adult subjects. Two marketed formulations of oxybutynin were used in the study: i) Ditropan IR®, which is immediate release (IR) oxybutynin; and ii) Ditropan XL® which is extended release (XL) oxybutynin. The total daily dose given was 20 mg. Solabegron was administered as tablets. Details of the solabegron tablet composition used are provided in Table 1 (composition A).

The first cohort (n=14 subjects) was given solabegron 200 mg BID (100 mg×2) alone for 5 days, this was followed in the second period by oxybutynin IR 5 mg QID alone for 5 days, and in the final dosing period a combination of solabegron 200 mg BID (100 mg×2) with oxybutynin IR 5 mg QID was administered for a period of 5 days.

A second cohort (n=12 subjects) was given solabegron 200 mg BID (100 mg×2) alone for 5 days, this was followed in the second period by oxybutynin XL 10 mg BID alone for 5 days, and in the final dosing period a combination of solabegron 200 mg BID (100 mg×2) with oxybutynin XL 10 mg BID was administered for a 5 day period.

Each study session was separated by a washout period of at least 5 days. Safety assessments included vital signs, ambulatory blood pressure monitoring (ABPM) physical examinations, clinical laboratory safety tests, 12-lead ECGs, PVR volume, to assess the potential for urinary retention, and adverse events. PVR was also utilized as a biomarker of bladder smooth muscle relaxation to determine if solabegron combined with oxybutynin had a greater effect on relaxation than either compound alone in healthy subjects.

Finally, blood samples were collected for pharmacokinetic analysis of plasma concentrations of, as appropriate: solabegron and its primary active metabolite as shown below; R-oxybutynin, S-oxybutynin and the metabolites R-desethyl oxybutynin and S-desethyl oxybutynin as shown below.

Primary active metabolite of solabegron,

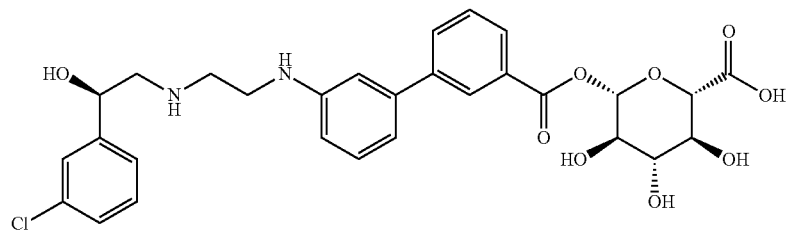 [SMILES: O=C(O[C@@H]1O[C@H](C(=O)O)[C@@H](O)[C@H](O)[C@H]1O)c1cccc(-c2cccc(NCCNC[C@H](O)c3cccc(Cl)c3)c2)c1]

Primary active metabolite of oxybutynin is desethyloxybutynin:

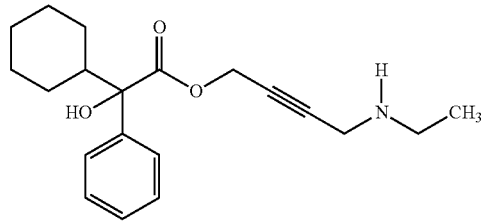 [SMILES: CCNCC#CCOC(=O)C(O)(c1ccccc1)C1CCCCC1]

TABLE 1

Solabegron Tablet Composition A

| COMPONENT | UNIT FORMULA (mg) | FUNCTION |
| --- | --- | --- |
| Wet Granulation Ingredients | | |
| (a) GW427353, B, ACTIVE SUBSTANCE | 110* | Active Ingredient |
| (b) MANNITOL 60 | 119.25 | Filler |
| (c) METHYLCELLULOSE, METHOCEL A15 PREMIUM LV | 10 | Binder |
| (d) CROSCARMELLOSE SODIUM | 10 | Disintegrant |
| (e) POLOXAMER F 68 | 2.5 | Surfactant |
| Extra granular Ingredients | | |
| (f) CROSCARMELLOSE SODIUM | 5 | Disintegrant |
| (g) MAGNESIUM STEARATE | 2.5 | Lubricant |
| (h) COLLOIDAL SILICON DIOXIDE | 0.75 | Glidant |
| Total | 250 | |

*100 mg after correction for purity and salt/base conversion.

Composition A was prepared by the blending and wet granulation of ingredients (a) through (e), Table 1, in a suitable high shear mixer/granulator. Ingredients (f) through (h) were added to the dried granulation, blended and compressed. Compressed tablets were covered with an aqueous film coat.

Results of the Drug Interaction Study—PVR Volume

Bladder ultrasound scans to measure PVR volumes were conducted on Day-1 (one day prior to the dosing period) and Day 6 (sixth day of the dosing period) of each study session.

Subjects dosed with solabegron alone or oxybutynin IR alone showed a mean increase from baseline of 4.4 mL and 45.7 mL in PVR volume respectively, while subjects dosed with the combination of solabegron and oxybutynin IR unexpectedly showed a mean increase from baseline of 79.8 mL. Subjects dosed with oxybutynin XL alone showed a mean increase from baseline of 20.2 mL in PVR volume while subjects dosed with the combination of solabegron and oxybutynin XL unexpectedly showed a mean increase from baseline of 50.8 mL in PVR volume. These data are summarized in Table 2.

TABLE 2

PVR data

| Active ingredient(s) administered | Mean increase from baseline (mL) |
| --- | --- |
| Solabegron | 4.4 |
| oxybutynin IR | 45.7 |
| oxybutynin XL | 20.2 |
| solabegron and oxybutynin IR | 79.8 |
| solabegron and oxybutynin XL | 50.8 |

These data indicate that in healthy subjects, solabegron given alone showed minimal changes in PVR volumes and oxybutynin IR or XL given alone showed modest changes in PVR volume, but solabegron and either oxybutynin IR or oxybutynin XL given in combination showed greater increases in PVR volumes in each case than is expected from an additive effect of the two active ingredients. When oxybutynin IR is used as the antimuscarinic, the PVR of the combination treatment is 79.8 mL versus 50.1 mL for the PVR sum of the individually administered drugs. Similarly, when oxybutynin XL is used as the antimuscarinic, the PVR of the combination treatment is 50.8 mL versus 24.6 mL for the PVR sum of the individually administered drugs. The latter comparison shows an increase of over 100% for the combination treatment versus the individual treatments.

This is interpreted as evidence of pharmacological synergism in the combination treatment, which indicates increased efficacy in treating one or more of the symptoms of OAB, since retaining more fluid in the PVR test indicates that the bladder muscles are more relaxed, thereby increasing bladder capacity.

Example 2. Effects of the Combination of Beta-Adrenoceptor Agonists and Antimuscarinics on Bladder Contractility in Rats Stimulation of efferent nerves to the urinary bladder results in the release of acetylcholine (ACh) that stimulates post-junctional muscarinic (M3) receptors on urinary bladder smooth muscle, resulting in contraction and subsequent urination. M2 receptors are functionally expressed in human bladder smooth muscle and may also play a role in bladder contractility, however most likely indirectly by enhancing M3 mediated contractions and inhibiting β-adrenoceptor mediated relaxation. Antimuscarinic drugs are believed to work primarily by blocking M3 receptors, thus inhibiting the contractions associated with overactive bladder.

Another approach to treating overactive bladder involves targeting β3-adrenoceptors, which are also located on urinary bladder smooth muscle. The stimulation of post-junctional β3-adrenoceptors results in the generation of cAMP and production of direct relaxation of bladder smooth muscle.

In order to investigate a possible pharmacological synergy on the combination of the muscarinic and the beta receptor pathways, the combination of the muscarinic antagonist oxybutynin and the beta-3 adrenoceptor agonist CL-316,243 (a very selective and potent rodent β3-AR agonist) was tested on EFS (electrical field stimulation)-induced responses in urinary bladder strips from rats.

Longitudinal strips of rat detrusor muscle were suspended in organ bath chambers containing oxygenated Krebs solution (pH 7.4, gassed with 95% $O_2$ and 5% $CO_2$ at 37° C.). Prazosin (1 μM) was added to the Krebs solution in order to block al-adrenoceptors. Bladder responses were measured using isometric transducers and recorded using a data acquisition system. Tissues were allowed to equilibrate under a resting tension of 1.0 g for 60 min. Following the equilibration period, strips were exposed to KCl (80 mM) to measure their viability. Tissues were washed and equilibrated for another 45 min period. Bladder strips were then subjected to EFS using the following parameters: maximal current 800 mA, frequency of 15 Hz, square pulse of 0.1 ms, trains of 4 s every 2 min. After approximately 15 min (when EFS contractions had stabilized), the selective β2-adrenoceptor antagonist ICI-118551 (30 nM) was incubated for 15 min. After stabilization of the contractile response, a concentration response curve was obtained for each bladder strip by adding CL-316,243 or oxybutynin (1 nM to 10 μM) (or corresponding vehicle) in log unit concentration increments.

In the first series of experiments it was determined that oxybutynin at a concentration of 10 nM produced a minimal contraction.

In a second series of experiments, a single concentration of oxybutynin at 10 nM (determined from the first series of experiments) was added to organ bath chambers followed by various doses of CL-316,243 to provide a concentration-response curve for CL-316,243.

In the presence of a minimally effective dose of oxybutynin, there was an approximate 3.5-fold shift to the left of concentration-response curve to CL-316,243. The $EC_{50}$ for inhibiting bladder contraction by CL-316,243 was 7.2 nM; however, in the presence of oxybutynin (10 nM) the $EC_{50}$ was 2.1 nM.

In addition, maximal inhibition of EFS-induced contractions by CL-316,243 alone was 65%, however in the presence of oxybutynin (10 nM) inhibition by CL-316,243 achieved 80% inhibition.

The differences in the $EC_{50}$ values and the inhibition of the maximal response were statistically significant (p<0.05).

These data indicate there was significant pharmacological synergy of the efficacy of inhibiting bladder contraction with the combination of an antimuscarinic agent with a selective beta-3 adrenoceptor agonist.

Example 3. Effects of the Combinations of Various Beta-Adrenoceptor Agonists and Antimuscarinics on Rat Bladder Contractions Induced by EFS (Electrical Field Stimulation)

In this study various combinations of β3-adrenoceptor agonists and antimuscarinics were tested in isolated rat urinary bladder strips.

Urinary bladder smooth muscle strips were obtained from female rats (Sprague-Dawley strain, body weight 240-360 g). Two strips per bladder were prepared and connected to tension transducers in 5 ml organ baths containing Krebs-Henseleit solution (kept at 37° C., pH 7.4, gassed with 95% $O_2$/5% $CO_2$). Prazosin (1 μM) was added to the Krebs solution in order to block al-adrenoceptors. Strips were equilibrated for at least 60 min at 1.0 g resting tension, during which tissues were washed every 15 min. Then, each strip was exposed to 80 mM KCl to verify its viability. After another 45 min wash-out period, strips were subjected to EFS (electrical field stimulation parameters: constant current 800 mA; frequency of 15 Hz; square pulse of 0.1 ms, train of 4 s every 2 min). After stabilization, ICI-118,551 (30 nM), a β2-adrenoceptor antagonist, was incubated for 15 min then 10 nM of oxybutynin, tolterodine, solifenacin, or their common solvent (vehicle control) were added to the strips for an additional 15 min. Cumulative concentrations of solabegron (10 nM-10 μM), mirabegron (10 nM-10 μM) and CL-316,243 (1 nM-10 μM) were then added in half-log increments. At the end of CRC's, 10 μM forskolin (FSK) was added to determine maximal relaxation (FIG. 1).

Results are displayed in FIGS. 2-5, and are expressed as % inhibition (mean±SEM) of basal EFS-induced contractions (EFS values obtained 15 min after addition of ICI-118,551).

Each CRC was fit using non-linear regression (GraphPad Prism® software) to obtain $E_{max}$ and $pIC_{50}$ ($-\log IC_{50}$) values. Mean CRCs for vehicle and treated strips were fit in parallel and statistically compared. The first fit was used to compare $E_{max}$ values and when these values were not statistically different, a second fit was performed, sharing $E_{max}$, in order to obtain $pIC_{50}$ values for each pair of curves. Differences were considered statistically significant when the null hypothesis could be rejected at a risk a of less than 0.05.

As evidenced by the data presented in the Figures, the $E_{max}$ values of CL-316,243 were significantly increased in the presence of oxybutynin and tolterodine. Further, the $IC_{50}$ of CL-316,243 was significantly decreased in the presence of oxybutynin.

For solabegron, the $E_{max}$ values were significantly increased by oxybutynin, tolterodine and solifenacin. Further, the $IC_{50}$ values of solabegron were significantly lower in the presence of oxybutynin and tolterodine. For mirabegron, the $E_{max}$ value appeared to be increased in the presence of tolterodine. Further, the $IC_{50}$ values of mirabegron were significantly lower in the presence of oxybutynin, tolterodine and solifenacin.

Thus, it is clear that antimuscarinics can affect both the potency and efficacy of beta-3 adrenergic receptor agonists.

What is claimed is:

1. A method of treating overactive bladder in a subject in need thereof, comprising administering a therapeutically effective amount of solabegron or a pharmaceutically-acceptable salt, pharmaceutically-acceptable derivative or zwitterion thereof, wherein treating overactive bladder is measured by an increase in voided volume.

2. The method of claim 1, wherein the solabegron is in a pharmaceutical composition comprising one or more pharmaceutically-acceptable carriers, diluents, or excipients.

3. The method of claim 1 wherein the pharmaceutically-acceptable salt is the hydrochloride salt.

4. The method of claim 1, wherein the solabegron is a zwitterion.

5. The method of claim 1 wherein the therapeutically effective amount of solabegron is between about 50 mg and about 800 mg.

6. The method of claim 1, further comprising alleviating one or more of the symptoms of overactive bladder selected from the group consisting of urinary urgency, frequency of mictruitions, nocturia, and urgency urinary incontinence, or a combination thereof.

7. A method of treating overactive bladder in a subject in need thereof, comprising administering a therapeutically effective amount of solabegron or a pharmaceutically-acceptable salt, pharmaceutically-acceptable derivative, or zwitterion thereof, wherein the voided volume of the subject is increased.

8. The method of claim 7, wherein the solabegron is in a pharmaceutical composition comprising one or more pharmaceutically-acceptable carriers, diluents, or excipients.

9. The method of claim 7, wherein the pharmaceutically-acceptable salt is the hydrochloride salt.

10. The method of claim 7, wherein the solabegron is a zwitterion.

11. The method of claim 7, wherein the therapeutically effective amount of solabegron is between about 50 mg and about 800 mg.

12. The method of claim 7, further comprising alleviating one or more of the symptoms of overactive bladder selected from the group consisting of urinary urgency, frequency of mictruitions, nocturia, and urgency urinary incontinence, or a combination thereof.

13. A method of treating overactive bladder in a subject in need thereof, comprising administering a combination comprising a therapeutically effective amount of solabegron or a pharmaceutically-acceptable salt, pharmaceutically-acceptable derivative, or zwitterion thereof; and a therapeutically effective amount, or a sub-therapeutically effective amount, of a muscarinic receptor antagonist or a pharmaceutically-acceptable salt, or pharmaceutically-acceptable derivative thereof, wherein treating overactive bladder is measured by an increase in voided volume.

14. The method of claim 13, wherein the solabegron is in a pharmaceutical composition comprising one or more pharmaceutically-acceptable carriers, diluents, or excipients.

15. The method of claim 13, wherein the muscarinic receptor antagonist is in a pharmaceutical composition comprising one or more pharmaceutically-acceptable carriers, diluents, or excipients.

16. The method of claim 13, wherein the muscarinic receptor antagonist is selected from a group consisting of oxybutynin, tolterodine, solifenacin, trospium, darifenacin, festerodine, hyoscyamine, and propiverine.

17. The method of claim 13, wherein the muscarinic receptor antagonist is oxybutynin.

18. The method of claim 13, wherein the solabegron is a hydrochloride salt.

19. The method of claim 13, wherein the solabegron is a zwitterion.

20. The method of claim 13, wherein the therapeutically effective amount of solabegron is about 50 mg to about 800 mg.

21. The method of claim 13, wherein the therapeutically effective amount of the muscarinic receptor antagonist is about 1 mg to about 90 mg.

22. The method of claim 13, wherein the sub-therapeutically effective amount of the muscarinic receptor antagonist is about 0.1 mg to about 50 mg.

23. The method of claim 13, wherein the solabegron and the muscarinic receptor antagonist are co-administered.

24. The method of claim 13, wherein the solabegron and the muscarinic receptor antagonist are contained in a single dosage form, wherein the single dosage form is a pharmaceutical composition.

25. The method of claim 13, wherein the solabegron and the muscarinic receptor antagonist are administered separately.

26. The method of claim 13, wherein there is a time delay between the administration of the solabegron and the muscarinic receptor antagonist.

27. The method of claim 13, further comprising alleviating one or more of the symptoms of overactive bladder selected from the group consisting of urinary urgency, frequency of mictruitions, nocturia, and urgency urinary incontinence, or a combination thereof.

28. A method of treating overactive bladder in a subject in need thereof, comprising administering a combination comprising a therapeutically effective amount of solabegron or a pharmaceutically-acceptable salt, pharmaceutically-acceptable derivative, or zwitterion thereof, and a therapeutically effective amount, or a sub-therapeutically effective amount, of a muscarinic receptor antagonist or a pharmaceutically-acceptable salt thereof, wherein the voided volume of the subject is increased.

29. The method of claim 28, wherein the solabegron is in a pharmaceutical composition comprising one or more pharmaceutically-acceptable carriers, diluents, or excipients.

30. The method of claim 28, wherein the muscarinic receptor antagonist is in a pharmaceutical composition comprising one or more pharmaceutically-acceptable carriers, diluents, or excipients.

31. The method of claim 28, wherein the muscarinic receptor antagonist is selected from a group consisting of oxybutynin, tolterodine, solifenacin, trospium, darifenacin, festerodine, hyoscyamine, and propiverine.

32. The method of claim 28, wherein the muscarinic receptor antagonist is oxybutynin.

33. The method of claim 28, wherein the solabegron is a hydrochloride salt.

34. The method of claim 28, wherein the solabegron is a zwitterion.

35. The method of claim 28, wherein the therapeutically effective amount of solabegron is about 50 mg to about 800 mg.

36. The method of claim 28, wherein the therapeutically effective amount of the muscarinic receptor antagonist is about 1 mg to about 90 mg.

37. The method of claim 28, wherein the sub-therapeutically effective amount of the muscarinic receptor antagonist is about 0.1 mg to about 50 mg.

38. The method of claim 28, wherein the solabegron and the muscarinic receptor antagonist are co-administered.

39. The method of claim 28, wherein the solabegron and the muscarinic receptor antagonist are contained in a single dosage form, wherein the single dosage form is a pharmaceutical composition.

40. The method of claim 28, wherein the solabegron and the muscarinic receptor antagonist are administered separately.

41. The method of claim 28, wherein there is a time delay between the administration of the solabegron and the muscarinic receptor antagonist.

42. The method of claim 28, further comprising alleviating one or more of the symptoms of overactive bladder selected from the group consisting of urinary urgency, frequency of mictruitions, nocturia, and urgency urinary incontinence, or a combination thereof.

* * * * *

UNITED STATES PATENT AND TRADEMARK OFFICE
CERTIFICATE OF CORRECTION

PATENT NO. : 9,907,767 B2
APPLICATION NO. : 15/323685
DATED : March 6, 2018
INVENTOR(S) : Stephen Caltabiano, Eliot Ohlstein and Stewart McCallum Page 1 of 1

It is certified that error appears in the above-identified patent and that said Letters Patent is hereby corrected as shown below:

On the Title Page

Item (63), should read:
Continuation-in-part of application no. PCT/US2015/038583, filed June 30, 2015; this application 15/323,685 is a continuation-in-part of 15/235,720, filed August 12, 2016, which is a continuation of 13/762,563, filed February 8, 2013, now Pat. No. 9,522,129, which is a continuation-in-part of 13/196,068, filed August 2, 2011, now Pat. No. 8,642,661.

Item (60), should read:
Provisional application No. 62/020,889, filed on July 3, 2014, provisional application No. 61/596,893, filed on February 9, 2012, provisional application No. 61/370,171, filed August 3, 2010.

Signed and Sealed this
Fifth Day of February, 2019

Andrei Iancu
*Director of the United States Patent and Trademark Office*